(12) United States Patent
Yasuda et al.

(10) Patent No.: US 12,147,651 B2
(45) Date of Patent: Nov. 19, 2024

(54) INFORMATION PROCESSING APPARATUS AND INFORMATION PROCESSING METHOD

(71) Applicant: Sony Group Corporation, Tokyo (JP)

(72) Inventors: Ryouhei Yasuda, Tokyo (JP); Yuhei Taki, Tokyo (JP); Hiro Iwase, Tokyo (JP); Kunihito Sawai, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 18/261,492

(22) PCT Filed: Jan. 6, 2022

(86) PCT No.: PCT/JP2022/000168
§ 371 (c)(1),
(2) Date: Jul. 14, 2023

(87) PCT Pub. No.: WO2022/158292
PCT Pub. Date: Jul. 28, 2022

(65) Prior Publication Data
US 2024/0069702 A1  Feb. 29, 2024

(30) Foreign Application Priority Data
Jan. 21, 2021  (JP) .................................. 2021-007751

(51) Int. Cl.
*G06F 3/04842*  (2022.01)
*G02B 27/01*  (2006.01)
(Continued)

(52) U.S. Cl.
CPC ....... *G06F 3/04842* (2013.01); *G02B 27/017* (2013.01); *G06F 3/013* (2013.01);
(Continued)

(58) Field of Classification Search
CPC ........ G06F 3/04842; G06F 3/013; G06F 3/16; G06F 30/00; G06F 2111/18; G02B 27/017; G06T 19/00
See application file for complete search history.

(56) References Cited

U.S. PATENT DOCUMENTS 9,335,547 B2 * 5/2016 Takano ................... G06F 3/013
9,721,396 B2 * 8/2017 Baba ..................... G06F 3/0488
(Continued)

FOREIGN PATENT DOCUMENTS

JP  2003-256859 A  9/2003
JP  2011-048522 A  3/2011
(Continued)

OTHER PUBLICATIONS

International Search Report and Written Opinion mailed on Apr. 12, 2022, received for PCT Application PCT/JP2022/000168, filed on Jan. 6, 2022, 10 pages including English Translation.

*Primary Examiner* — Michael J Jansen, II
(74) *Attorney, Agent, or Firm* — XSENSUS LLP

(57) ABSTRACT

An information processing apparatus according to the present disclosure includes: an acquisition unit that acquires a character string whose part of speech is to be estimated; and a generation unit that generates part-of-speech estimation information for estimating a part of speech of the character string based on a byte sequence obtained by converting the character string.

17 Claims, 18 Drawing Sheets

(51) Int. Cl.
  *G06F 3/01* (2006.01)
  *G06F 3/16* (2006.01)
  *G06F 30/00* (2020.01)
  *G06F 111/18* (2020.01)
  *G06T 19/00* (2011.01)
(52) U.S. Cl.
  CPC .............. *G06F 3/16* (2013.01); *G06F 30/00* (2020.01); *G06F 2111/18* (2020.01); *G06T 19/00* (2013.01)

(56) References Cited

U.S. PATENT DOCUMENTS

| | | | | |
|---|---|---|---|---|
| 9,807,361 | B2* | 10/2017 | Kato | H04N 13/106 |
| 9,823,815 | B2* | 11/2017 | Yasuda | B60K 35/00 |
| 10,013,812 | B2* | 7/2018 | Muta | A63F 13/525 |
| 10,115,235 | B2* | 10/2018 | Inomata | G06T 19/006 |
| 10,198,855 | B2* | 2/2019 | Terahata | G02B 27/017 |
| 10,496,186 | B2* | 12/2019 | Yasuda | G06F 3/16 |
| 10,539,797 | B2* | 1/2020 | Nakashima | G02B 27/017 |
| 11,175,737 | B2* | 11/2021 | Hagiwara | G06V 10/235 |
| 11,176,747 | B2* | 11/2021 | Ishihara | G06F 3/011 |
| 11,282,264 | B2* | 3/2022 | Chen | G06T 15/04 |
| 11,282,481 | B2* | 3/2022 | Furuta | G09G 5/38 |
| 2011/0050686 | A1* | 3/2011 | Nojima | G06F 3/04815 |
| | | | | 345/419 |
| 2014/0285404 | A1* | 9/2014 | Takano | G06F 3/04812 |
| | | | | 345/8 |
| 2014/0285641 | A1* | 9/2014 | Kato | G06T 19/00 |
| | | | | 348/54 |
| 2015/0253939 | A1* | 9/2015 | Yasuda | G06F 3/0482 |
| | | | | 715/810 |
| 2016/0089980 | A1* | 3/2016 | Kurahashi | G06V 20/597 |
| | | | | 345/156 |
| 2017/0024935 | A1* | 1/2017 | Baba | G06F 3/0308 |
| 2017/0098330 | A1* | 4/2017 | Inomata | G06F 3/04815 |
| 2017/0263058 | A1* | 9/2017 | Muta | G06F 3/011 |
| 2018/0003979 | A1* | 1/2018 | Nakashima | G02B 27/017 |
| 2018/0025531 | A1* | 1/2018 | Terahata | G06T 15/20 |
| | | | | 345/421 |
| 2018/0059812 | A1* | 3/2018 | Inomata | G06F 3/011 |
| 2018/0129303 | A1* | 5/2018 | Yasuda | A63F 13/219 |
| 2019/0355170 | A1* | 11/2019 | Chen | G06F 3/147 |
| 2020/0335065 | A1* | 10/2020 | Furuta | G06F 3/013 |
| 2020/0342671 | A1* | 10/2020 | Ishihara | G06F 3/011 |
| 2021/0034150 | A1* | 2/2021 | Hagiwara | G06V 40/18 |
| 2022/0129069 | A1* | 4/2022 | Yasuda | G06F 3/0487 |
| 2024/0069702 | A1* | 2/2024 | Yasuda | G02B 27/017 |

FOREIGN PATENT DOCUMENTS

| | | |
|---|---|---|
| WO | 2014/057618 A1 | 4/2014 |
| WO | 2020/189254 A1 | 9/2020 |

* cited by examiner

INFORMATION PROCESSING APPARATUS AND INFORMATION PROCESSING METHOD

CROSS-REFERENCE TO RELATED APPLICATIONS

The present application is based on PCT filing PCT/JP2022/000168, filed Jan. 6, 2022, which claims priority to Japanese Application No. 2021-007751, filed Jan. 21, 2021, the entire contents of each are incorporated herein by reference.

FIELD

The present disclosure relates to an information processing apparatus and an information processing method.

BACKGROUND

In recent years, with the development of sensing technology, methods for giving input to and performing control on devices have been diversified. For example, a technique related to an operation of selecting a target such as an icon by using a line of sight of a user is known (e.g., Patent Literature 1).

CITATION LIST

Patent Literature

Patent Literature 1: WO 2020/189254 A

SUMMARY

Technical Problem

Unfortunately, when a target is selected based on a line of sight of a user as in a conventional technique, unstableness of the line of sight of the user and the like makes it difficult to appropriately select the target. Therefore, it is desired to flexibly select the target in accordance with the line of sight of the user.

Thus, the present disclosure proposes an information processing apparatus and an information processing method capable of flexibly selecting a target in accordance with a line of sight of a user.

Solution to Problem

According to the present disclosure, an information processing apparatus includes an acquisition unit that acquires line-of-sight information indicating a gaze point of a user and object information indicating a plurality of objects; and a selection unit that selects one object from the plurality of objects based on a positional relation between the gaze point of the user and the plurality of objects.

DESCRIPTION OF EMBODIMENTS

An embodiment of the present disclosure will be described in detail below with reference to the drawings. Note that an information processing apparatus and an information processing method according to the present application are not limited by the embodiment. Furthermore, in the following embodiment, the same reference signs are attached to the same parts to omit duplicate description.

The present disclosure will be described in the following item order.

1. Embodiment
 1-1. Outline of Information Processing According to Embodiment of Present Disclosure
  1-1-1. Background, Effects, and the Like
 1-2. Configuration of Information Processing Apparatus According to Embodiment
 1-3. Procedure of Information Processing According to Embodiment
 1-4. Processing Example
  1-4-1. Area Selection Example
  1-4-2. Example of Selection Made by Designating Range
  1-4-3. Example of Continuously Selecting Partial Areas
  1-4-4. Example of Change in Selection Width
  1-4-5. Editing Example
   1-4-5-1. Change of Selected Point
   1-4-5-2. Addition of Point 1-4-6. Multiple Layer Example
1-4-6-1. Selection Example 1 (Medical Image)
1-4-6-2. Selection Example 2 (Map)
1-4-6-3. Selection Example 3 (Article)
2. Other Embodiments
2-1. Variation
2-2. Other Configuration Examples
2-3. Others
3. Effects According to Present Disclosure
4. Hardware Configuration

1. Embodiment

[1-1. Outline of Information Processing According to Embodiment of Present Disclosure]

Figure 1:
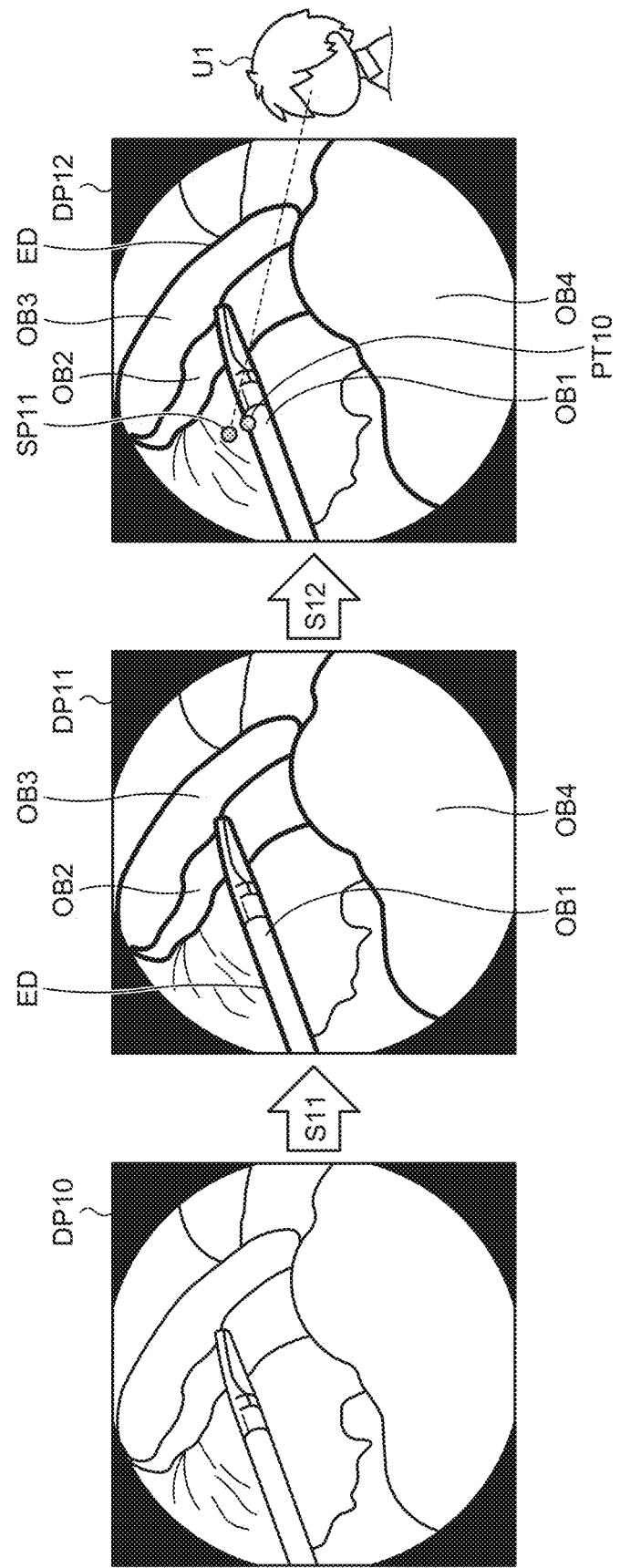
FIG. 1 illustrates one example of information processing according to an embodiment of the present disclosure.
Figure 2:
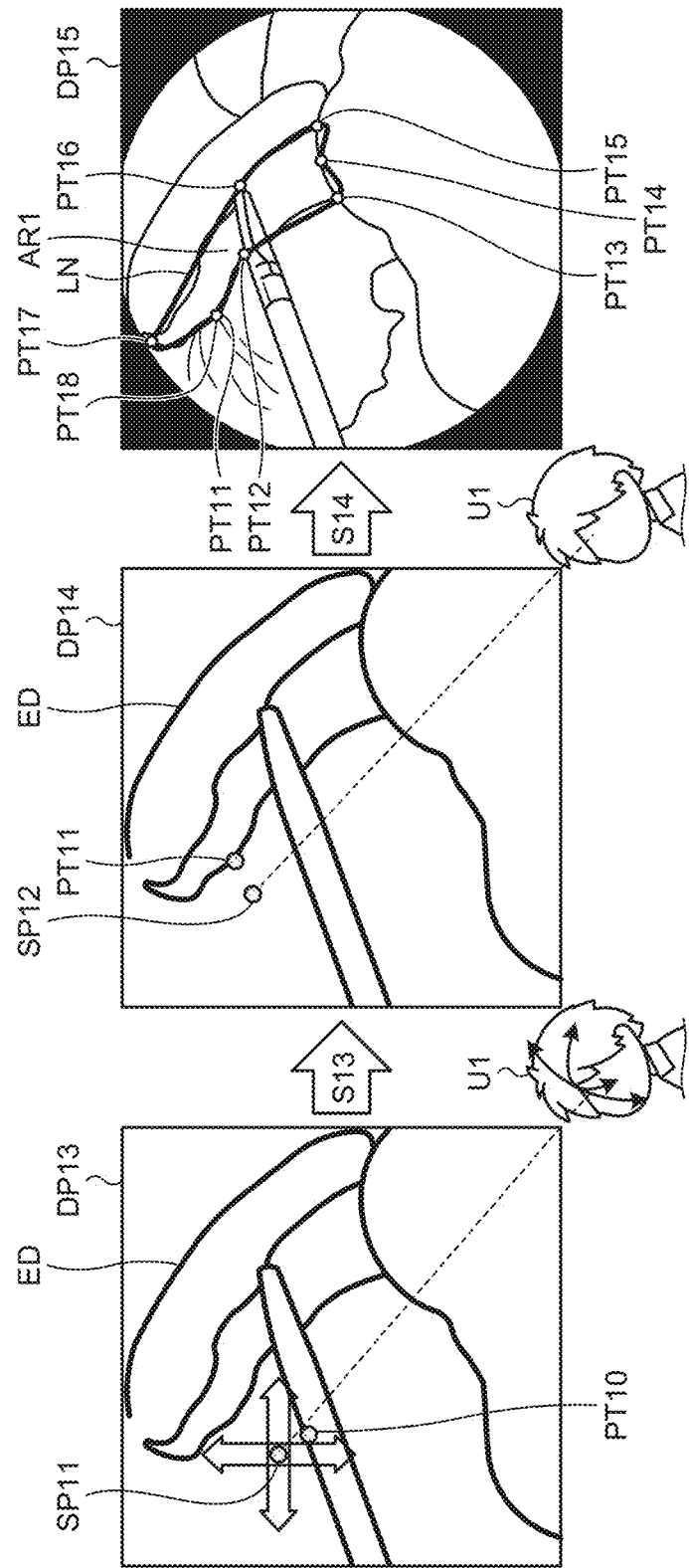
FIG. 2 illustrates one example of the information processing according to the embodiment of the present disclosure.

FIGS. 1 and 2 illustrate one example of information processing according to the embodiment of the present disclosure. Specifically, FIG. 1 illustrates one example of processing of selecting (selection processing) a point on a boundary (edge) of an object (target) based on the boundary of the object and a gaze point of a user U1. Furthermore, FIG. 2 illustrates an outline of processing related to determination (generation) of an area made by changing an object selected based on a change in the gaze point of the user U1 and selecting a plurality of points.

Figure 3:
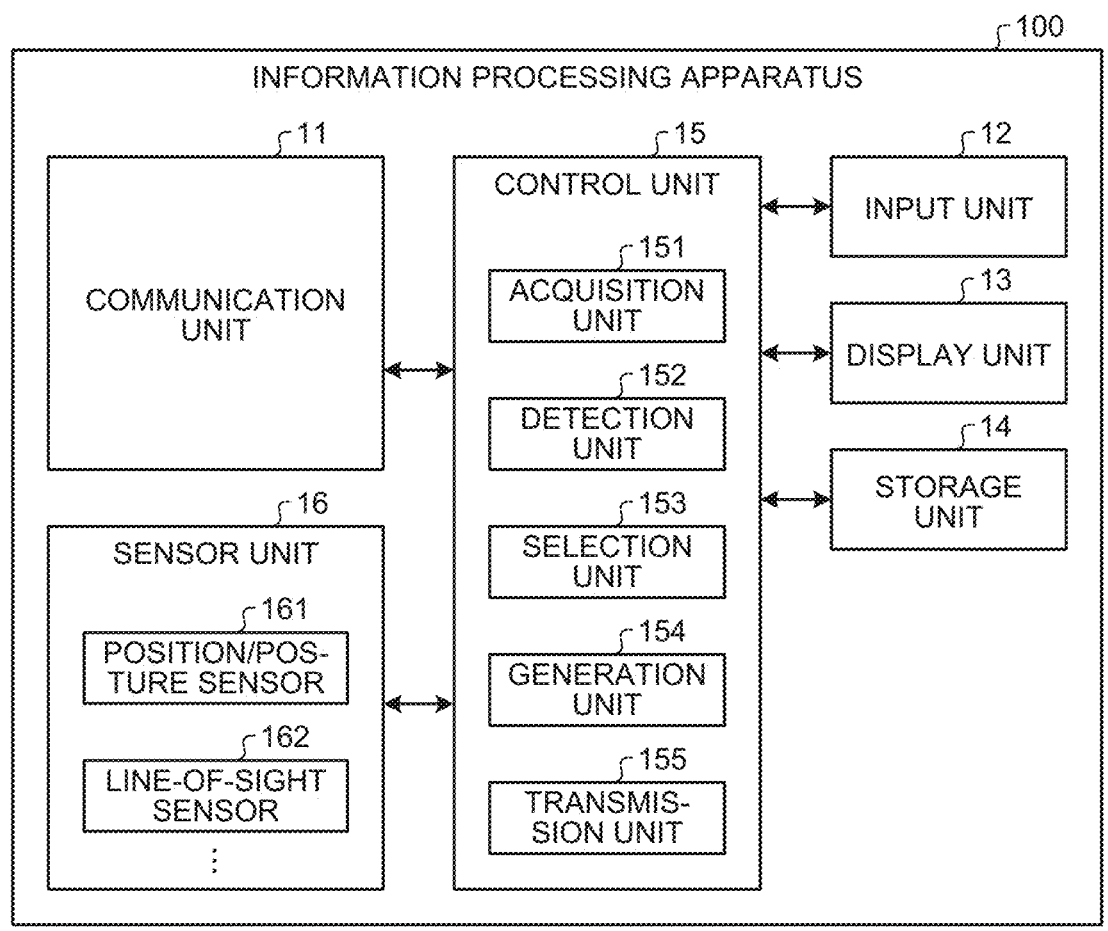
FIG. 3 illustrates a configuration example of an information processing apparatus according to the embodiment of the present disclosure.

An information processing apparatus 100 in FIG. 3 performs the information processing according to the embodiment of the present disclosure. The information processing apparatus 100 in FIG. 3 is one example of an information processing apparatus that performs selection processing and processing of determining (generating) an area based on a plurality of selected points and the like. The information processing apparatus 100 executes the information processing according to the embodiment. For example, the information processing apparatus 100 is a terminal device used by a user.

The information processing apparatus 100 is a computer that executes processing of selecting one object from a plurality of objects based on the positional relation between the gaze point of the user and the plurality of objects. Furthermore, the information processing apparatus 100 selects one area from a plurality of areas based on the positional relation between the gaze point of the user and the plurality of areas.

FIG. 1 illustrates an example in which the information processing apparatus 100, which is a terminal device used by a user, performs selection processing and the like. In this case, the information processing apparatus 100 is a device apparatus used by the user. The information processing apparatus 100 receives input from the user. For example, the information processing apparatus 100 receives input given by a line of sight of the user, speech input given by an utterance of the user, and input given by user operation. The information processing apparatus 100 displays information in accordance with user input. The information processing apparatus 100 may be any apparatus as long as the apparatus can perform the processing in the embodiment. For example, the information processing apparatus 100 may include a smartphone, a smart speaker, a television, a tablet terminal, a notebook personal computer (PC), a desktop PC, a mobile phone, and a personal digital assistant (PDA). The information processing apparatus 100 may be a wearable device worn by the user and the like. For example, the information processing apparatus 100 may include various apparatuses such as a head-mounted display, virtual reality (VR) goggles integrated with a headset, VR goggles fitted in a smartphone, and a wearable device integrated with glasses, earphones, or the like.

Furthermore, the information processing apparatus 100 may include software modules for speech signal processing, speech recognition, utterance semantic analysis, and dialogue control, for example. The information processing apparatus 100 may have a function of speech recognition. For example, the information processing apparatus 100 may have functions of natural language understanding (NLU) and automatic speech recognition (ASR). For example, the information processing apparatus 100 may estimate information on the intent (intention) and entity (target) of the user from input information given by an utterance of the user. The information processing apparatus 100 functions as a speech recognition server having functions of the natural language understanding and the automatic speech recognition.

Note that a device that performs selection processing to be described below is not limited to the terminal device used by the user, and may be any device. For example, the information processing apparatus that performs the selection processing and the terminal device used by the user may be separate from each other. Note that a system configuration and the like in a case where the selection processing is performed on the server side will be described later.

Details of the example in FIGS. 1 and 2 will now be described. Note that, although, in the example of FIGS. 1 and 2, a case where selection processing is performed by using a surgical image (surgical video) as an image (content) to be processed will be described in one example, the image (content) to be processed is not limited to the surgical image, and may be images (content) of various types. For example, various images (content) such as a map image (content) and a product image (content) may be processed, and examples thereof will be described later.

First, in the example of FIG. 1, the information processing apparatus 100 displays a surgical image (surgical video) such as an image DP10. Note that the information processing apparatus 100 may capture a surgical image such as the image DP10 with an image sensor (camera) of a sensor unit 16, or may acquire (receive) a surgical image such as the image DP10 captured by another sensor device (e.g., endoscope camera) from another device.

Then, the information processing apparatus 100 executes edge detection of a surgical image such as the image DP10 (Step S11). A detection unit 152 detects a boundary in the image DP10 and the like by appropriately using an edge detection technique. Note that the detection unit 152 detects a boundary by using an algorithm of not only the edge detection but segmentation detection, a depth map, or the like. Since the information processing apparatus 100 detects a boundary by using the above-described known technique, detailed description will be omitted.

In the example of FIG. 1, the information processing apparatus 100 detects boundaries ED (e.g., corresponding to thick line portions in image DP11) as illustrated in the image DP11 by performing the edge detection. That is, the information processing apparatus 100 automatically detects an edge (boundary) from an image. Then, the information processing apparatus 100 divides the image DP11 into a plurality of objects such as objects OB1, OB2, OB3, and OB4 by using the detected boundaries ED. For example, in the image DP11, the object OB1 is a forceps, which is a surgical instrument, and the objects OB2 to OB4 and the like indicate organs of a patient.

The information processing apparatus 100 selects one object from the plurality of objects OB1 to OB4 and the like based on the positional relation between a gaze point of the user U1, who is a doctor (e.g., surgeon) performing surgery, and the plurality of objects OB1 to OB4 and the like (Step S11). For example, the information processing apparatus 100 selects a point on a boundary ED closest to the gaze point of the user U1 among the boundaries ED that separate the plurality of objects OB1 to OB4 and the like. Note that, although a case where the gaze point of the user is displayed is described in one example, the gaze point of the user is not required to be displayed.

This causes the information processing apparatus 100 to select one object, which is an object closest to the gaze point of the user U1. In the example of FIG. 1, as illustrated in an image DP12, the information processing apparatus 100 selects a point PT10, which is a point on the boundary ED closest to a gaze point SP11 of the user U1. That is, the information processing apparatus 100 selects the object OB1, which is the forceps. In this manner, the information processing apparatus 100 can flexibly select a target in accordance with a line of sight of the user.

A change in selecting a point on a boundary ED by changing the position of the gaze point of the user U1 will now be described with reference to FIG. 2. Note that a case where a point which the user U1 desires to select is not the boundary of the object OB1 but the boundary of the object OB2 will be described below in one example. In FIG. 2, in order to describe a change of a point selected (also referred to as "selected point") by a change in the line of sight of the user U1, illustration of a portion of a surgical image will be omitted, and only a boundary ED indicating an edge detected from the surgical image is illustrated in images DP13 and DP14, but the images DP13 and DP14 also include the surgical image.

As illustrated in the image DP13, the information processing apparatus 100 changes the position of the selected point in accordance with the change in the line of sight of the user U1 (Step S12). For example, the user U1 may change the position of the line of sight (gaze point) by moving only the eyes, or may change the position of the line of sight (gaze point) by changing the position or posture of the head. For example, the user U1 may change the line of sight (gaze point) by continuously adjusting the position in a head direction. In the example of FIG. 2, since the user U1 desires to select the object OB2, the user U1 changes the position to the line of sight in a direction approaching the object OB2.

In response to the change in the position of the gaze point of the user U1, the information processing apparatus 100 selects a point on the boundary ED closest to the gaze point of the user U1 among the boundaries ED (Step S13). The user U1 makes an adjustment so that a desired boundary ED is selected, and decides the position of the point. In the example of FIG. 2, as illustrated in the image DP14, the information processing apparatus 100 selects a point PT11, which is a point on the boundary ED closest to a gaze point SP12 of the user U1 after the position change. In this manner, the information processing apparatus 100 selects the object OB2, which is an object of a part of an organ desired by the user U1 to be selected.

The user U1 confirms that the point PT11 on the boundary ED in accordance with the object OB2 desired to be selected has been selected. Then, the user U1 performs an operation for determining (deciding) the point PT11 as the selected point (also referred to as "determination operation"). For example, as illustrated in the image DP14, the user U1 performs the determination operation of setting the point PT11 as a selected point that has been determined (also referred to as "determined selected point") by issuing an utterance such as "select this point" and "select here" with the point PT11 being displayed. In this case, the information processing apparatus 100 determines (decides) the point PT11 as the selected point (determined selected point) in response to detection of the utterance of the user U1, such as "select this point" and "select here". This causes the point PT11 determined as the selected point to be continuously displayed.

The information processing apparatus 100 selects a plurality of points on the boundary ED in response to movements of the gaze point of the user U1 (Step S14). The information processing apparatus 100 determines (decides) a plurality of determined selected points in response to operations of the user U1 as described above. In the example of FIG. 2, the information processing apparatus 100 selects eight points in the ascending order of the numbers of reference signs "PT*" (* is any number) added to points, that is, in the order of points PT11, PT12, PT13, PT14, PT15, PT16, PT17, and PT18. For example, as illustrated in an image DP15, the information processing apparatus 100 determines (decides) eight determined selected points of points PT11 to PT18. Note that, since the point PT11, which is the first determined point (also referred to as "start point") among the determined selected points, overlaps the point PT18, which is the last determined point (also referred to as "end point") among the determined selected points (e.g., at same position), the image DP15 illustrates seven points.

Here, when the selected start point and end point overlap each other, the information processing apparatus 100 generates an area by connecting a plurality of selected points (determined selected points). For example, the information processing apparatus 100 connects the points with a line in the order in which the points are set as determined selected points. When the start point and the end point overlap each other (e.g., coincide with each other), the information processing apparatus 100 generates an area, which is formed by the line connecting the determined selected points. In the example of FIG. 2, as illustrated in the image DP15, the information processing apparatus 100 generates an area AR1 having, as a boundary, a line LN connecting the plurality of points PT11 to PT18 by connecting the plurality of points PT11 to PT18 in the selected order with the line. In this manner, the information processing apparatus 100 can select (generate) a desired area by selecting points based on the line of sight of the user.

Note that, although, in the example of FIG. 2, for the sake of description, a case where the line LN connecting the plurality of points PT11 to PT18 is a curve has been described in one example, the line LN connecting the plurality of points PT11 to PT18 is not limited to a curve, and may be a line of any form, such as a straight line and a broken line. For example, the information processing apparatus 100 may receive user designation regarding a shape of a line connecting selected points. For example, the information processing apparatus 100 may allow the user to designate the shape of a line connecting selected points by a speech.

In this case, when the user U1 utters "select an area with a straight line", the information processing apparatus 100 may set the form of the line LN to a straight line. Furthermore, when the user U1 utters "select an area with a curve", the information processing apparatus 100 may set the form of the line LN to a curve similarly to the case of FIG. 2. In this case, the information processing apparatus 100 may set the line LN to a curve along the boundary ED. Furthermore, the information processing apparatus 100 may set the line LN to a curve connecting a plurality of points along a movement route of the line of sight of the user U1. Furthermore, when the user U1 utters "select an area with a wavy line", the information processing apparatus 100 may set the form of the line LN to a wavy line.

Note that the above is merely one example, and any form of the line LN can be adopted. Furthermore, when the user U1 does not desire to select an edge (point on boundary ED), the information processing apparatus 100 may allow the user U1 to select a point by free pointing by the user U1 uttering "select freely". For example, when a point is selected by free pointing, the information processing apparatus 100 may set the position of the gaze point of the user U1 as a selected point.

[1-1-1. Background, Effects, and the Like]

Conventionally, for example, an area can be set by a handsfree operation by designating a plurality of points using a speech command, line-of-sight detection, and head-direction detection. It is, however, difficult to draw a curve as intended and set a complicated shape. Furthermore, an error in line-of-sight detection and head-direction detection has made it difficult to strictly designate a desired location.

Therefore, when a position is designated by a line of sight or a head direction, the information processing apparatus 100 abstracts boundary line information given by an edge, segmentation, a depth map, and the like from a field-of-view video, and enables the user to select a desired target such as a point on a boundary (edge) accordingly. This enables the information processing apparatus 100 to easily set a shape closer to an intention than before at the time when an object or an area of the field-of-view video is selected in a handsfree manner. In this manner, when an area is selected in the handsfree manner, the information processing apparatus 100 can easily set a desired shape by using a feature point of the field-of-view video even if accuracies of a line of sight and a head direction are not sufficient.

[1-2. Configuration of Information Processing Apparatus According to Embodiment]

Next, a configuration of the information processing apparatus 100 will be described. The information processing apparatus 100 is one example of an information processing apparatus that executes information processing according to the embodiment. FIG. 3 illustrates a configuration example of the information processing apparatus 100 according to the embodiment of the present disclosure. For example, the information processing apparatus 100 in FIG. 3 is one example of the information processing apparatus. The information processing apparatus 100 is a computer that implements a function of an information processing apparatus to be described later.

As illustrated in FIG. 3, the information processing apparatus 100 includes a communication unit 11, an input unit 12, a display unit 13, a storage unit 14, a control unit 15, and the sensor unit 16. In the example of FIG. 3, the information processing apparatus 100 includes the input unit 12 (e.g., keyboard and mouse) and the display unit 13 (e.g., liquid crystal display). The input unit 12 receives various operations from an administrator and the like of the information processing apparatus 100. The display unit 13 displays various pieces of information.

The communication unit 11 is implemented by, for example, a network interface card (NIC) and a communication circuit. The communication unit 11 is connected to a communication network N (network such as Internet) by wire or wirelessly, and transmits and receives information to and from another device and the like via the communication network N.

The user inputs various operations to the input unit 12. The input unit 12 receives input from the user. The input unit 12 receives input given by an utterance (speech) of the user. For example, the input unit 12 receives user input given by a speech via a speech sensor such as a microphone of the sensor unit 16. The input unit 12 receives various operations given by an utterance of the user. Furthermore, for example, the input unit 12 may receive an operation given by a gesture of the user with a motion sensor and the like that detects a gesture of the user and the like. In this case, the sensor unit 16 includes the motion sensor. Furthermore, the input unit 12 may receive various operations from the user via a keyboard, a mouse, or a touch panel provided in the information processing apparatus 100.

The display unit 13 displays various pieces of information. The display unit 13 is a display device (display unit) such as a display, and displays various pieces of information. The display unit 13 displays information of a detection result from the detection unit 152. The display unit 13 displays information selected by a selection unit 153. The display unit 13 displays information generated by a generation unit 154.

Furthermore, the information processing apparatus 100 may have not only the display unit 13 but a functional configuration that outputs information. Note that the information processing apparatus 100 may have a function of outputting information as a speech. For example, the information processing apparatus 100 may include a speech output unit that outputs a speech, such as a speaker.

The storage unit 14 is implemented by, for example, a semiconductor memory element, such as a random access memory (RAM) and a flash memory, or a storage device, such as a hard disk and an optical disk. The storage unit 14 stores various pieces of information necessary for processing. For example, the storage unit 14 stores various pieces of information such as information necessary for displaying information such as an image and information necessary for selection processing. The storage unit 14 stores information of an edge detection result. For example, the storage unit 14 stores information to be displayed based on a detection result, such as the boundary ED.

For example, the storage unit 14 stores images to be subjected to edge detection, point selection, area selection, area generation, and the like. For example, the storage unit 14 stores various images such as a surgical image (surgical video). For example, the storage unit 14 stores information on the position of a selected point such as a selected point and a determined selected point. For example, the storage unit 14 stores information on the arrangement of a line connecting a plurality of selected points. Furthermore, for example, the storage unit 14 stores information on the arrangement of an area such as a selected area and a generated area. Note that the above is merely one example, and the storage unit 14 stores various pieces of information necessary for displaying (presenting) information to the user.

Furthermore, for example, the storage unit 14 stores information of a speech recognition application (program) that implements a speech recognition function. For example, the information processing apparatus 100 can recognize a speech by activating the speech recognition application (also simply referred to as "speech recognition"). The storage unit 14 stores various pieces of information used for speech recognition. The storage unit 14 stores information of a dictionary used for a speech recognition dictionary (speech recognition dictionary). The storage unit 14 stores information of a plurality of speech recognition dictionaries.

The control unit 15 is implemented by, for example, a central processing unit (CPU) and a micro processing unit (MPU) executing a program (e.g., information processing program according to present disclosure) stored in the information processing apparatus 100 using a random access memory (RAM) or the like as a work area. Furthermore, the control unit 15 is a controller, and may be implemented by an integrated circuit such as an application specific integrated circuit (ASIC) and a field programmable gate array (FPGA).

As illustrated in FIG. 3, the control unit 15 includes an acquisition unit 151, the detection unit 152, the selection unit 153, the generation unit 154, and a transmission unit 155, and implements or executes a function and an action of information processing to be described below. Note that the internal configuration of the control unit 15 is not limited to the configuration in FIG. 3. Another configuration may be adopted as long as the configuration performs the information processing to be described later.

The acquisition unit 151 acquires various pieces of information. The acquisition unit 151 acquires various pieces of information from an external information processing apparatus. The acquisition unit 151 acquires various pieces of information from the storage unit 14. The acquisition unit 151 acquires information received by the input unit 12.

The acquisition unit 151 acquires various pieces of information detected by the detection unit 152. The acquisition unit 151 acquires various pieces of information selected by the selection unit 153. The acquisition unit 151 acquires various pieces of information generated by the generation unit 154. The acquisition unit 151 acquires sensor information detected by the sensor unit 16.

The acquisition unit 151 acquires line-of-sight information and object information. The line-of-sight information indicates a gaze point of the user. The object information indicates a plurality of objects. The acquisition unit 151 acquires object information indicating boundaries of a plurality of objects. The acquisition unit 151 acquires object information indicating boundaries of a plurality of objects detected from an image. The acquisition unit 151 acquires object information indicating boundaries of a plurality of objects detected from a plurality of images.

The acquisition unit 151 acquires the line-of-sight information and area information. The line-of-sight information indicates a gaze point of the user. The area information indicates a plurality of areas based on the arrangement of the objects. The acquisition unit 151 acquires area information indicating a plurality of areas based on boundaries of the objects. The acquisition unit 151 acquires designation information indicating designation of the user for a plurality of partial areas. The acquisition unit 151 acquires designation information indicating designation given by a line of sight of the user for a plurality of partial areas. The acquisition unit 151 acquires designation information indicating designation of a range in one area given by a line of sight of the user.

The detection unit 152 performs detection processing. The detection unit 152 detects various pieces of information. The detection unit 152 detects various pieces of information based on information acquired from an external information processing apparatus. The detection unit 152 detects various pieces of information based on information stored in the storage unit 14.

The detection unit 152 detects various pieces of information from an image by appropriately using a technique such as image analysis. The detection unit 152 detects a boundary in an image by appropriately using a technique such as image analysis. The detection unit 152 detects a boundary by appropriately using an edge detection technique. Note that the detection unit 152 detects a boundary by using an algorithm of not only the edge detection but segmentation detection, a depth map, or the like.

The selection unit 153 performs selection processing. The selection unit 153 performs various selections. The selection unit 153 selects various pieces of information based on the information stored in the storage unit 14. The selection unit 153 selects various pieces of information based on information acquired by the acquisition unit 151. The selection unit 153 selects various pieces of information based on information detected by the detection unit 152.

The selection unit 153 makes various judgments. The selection unit 153 makes various judgments based on the information stored in the storage unit 14. The selection unit 153 makes various judgments based on the information acquired by the acquisition unit 151. The selection unit 153 makes various judgments based on the information detected by the detection unit 152.

The selection unit 153 selects one object from a plurality of objects based on the positional relation between a gaze point of the user and the plurality of objects. The selection unit 153 selects one object, which is an object closest to the gaze point of the user.

The selection unit 153 selects a point on a boundary closest to the gaze point of the user in the boundary of the one object. The selection unit 153 selects a plurality of points on the boundary of the one object in accordance with movements of the gaze point of the user.

The selection unit 153 selects one area from a plurality of areas based on the positional relation between the gaze point of the user and the plurality of areas. The selection unit 153 selects one area, which is an area where the gaze point of the user is located, from the plurality of areas.

The selection unit 153 selects one area corresponding to an object in the boundary of which the gaze point of the user is located. The selection unit 153 selects the one area as an area to be processed in relation to editing.

The selection unit 153 selects a partial area designated by the user from a plurality of partial areas. The selection unit 153 selects a partial area designated by the user based on a line of sight of the user. The selection unit 153 selects a partial area located within the range from the plurality of partial areas.

The generation unit 154 performs generation processing of generating various pieces of information. The generation unit 154 generates various pieces of information based on the information stored in the storage unit 14. The generation unit 154 generates various pieces of information based on the information acquired by the acquisition unit 151. The generation unit 154 generates various pieces of information based on the information selected by the selection unit 153. The generation unit 154 generates an image indicating an edge detection result.

The generation unit 154 generates an area having, as a boundary, a line connecting a plurality of points by connecting the plurality of points in the selected order with the line. The generation unit 154 changes the area by changing the position of one of the plurality of points. The generation unit 154 changes the area by adding a new point to the plurality of points.

The generation unit 154 generates a mesh that divides one area into a plurality of partial areas. The generation unit 154 generates a mesh that divides one area into a plurality of partial areas having a rectangular shape.

The generation unit 154 may generate various pieces of information to be displayed on the display unit 13. The generation unit 154 may generate various pieces of information such as character information to be displayed on the display unit 13 and image information including a graph. In this case, the generation unit 154 generates information (image) on a screen by appropriately using various conventional techniques related to the image. The generation unit 154 generates an image by appropriately using various conventional techniques related to a GUI. For example, the generation unit 154 may generate an image by using CSS, JavaScript (registered trademark), HTML, or any language in which information processing such as the above-described information display and operation reception can be written.

The transmission unit 155 transmits various pieces of information. The transmission unit 155 provides various pieces of information. The transmission unit 155 provides various pieces of information to an external information processing apparatus. The transmission unit 155 transmits various pieces of information to an external information processing apparatus. The transmission unit 155 transmits the information stored in the storage unit 14. The transmission unit 155 transmits the information acquired by the acquisition unit 151. The transmission unit 155 transmits a detection result from the detection unit 152. The transmission unit 155 transmits the information selected by the selection unit 153. The transmission unit 155 transmits the information generated by the generation unit 154.

Note that each of pieces of processing performed by the above-described control unit 15 may be performed by, for example, JavaScript (registered trademark). Furthermore, when the above-described processing such as information processing performed by the control unit 15 is performed by a predetermined application, each unit of the control unit 15 may be implemented by, for example, the predetermined application. For example, processing such as information processing performed by the control unit 15 may be performed by control information received from an external information processing apparatus. For example, when the above-described display processing is performed by a predetermined application (e.g., information output app), the control unit 15 may include, for example, an app control unit that controls the predetermined app and a dedicated app.

The sensor unit 16 includes a sensor that detects various sensors. In the example of FIG. 3, the sensor unit 16 includes a position/posture sensor 161 and a line-of-sight sensor 162. Furthermore, the sensor unit 16 includes a speech sensor that detects a speech, such as a microphone.

The position/posture sensor 161 detects the position and posture of the user with a camera, a gyro sensor, and the like. For example, the position/posture sensor 161 detects the position and posture of the head of the user. For example, the position/posture sensor 161 detects a change in the position and posture of the head of the user by using an image of the head of the user captured by a camera. Note that the position/posture sensor 161 may have any configuration as long as the configuration can detect the state of the head of the user necessary for processing.

The line-of-sight sensor 162 detects a line of sight of the user. The line-of-sight sensor 162 detects a direction of a line of sight of the user by using an eye tracking technique based on detection results from a camera, an optical sensor, a motion sensor, and the like (all not illustrated) mounted on a terminal device 10, for example. The line-of-sight sensor 162 decides a gaze area at which the user is gazing on the screen based on the detected line-of-sight direction. The line-of-sight sensor 162 transmits line-of-sight information including the decided gaze area to the information processing apparatus 100. Note that the above is merely one example, and the line-of-sight sensor 162 may have any configuration as long as the configuration can detect information on a line of sight of the user necessary for processing.

Note that the sensor unit 16 includes various sensors in addition to the position/posture sensor 161 and the line-of-sight sensor 162. The sensor unit 16 includes a sensor (biological signal sensor) for detecting a biological signal from the user. For example, the terminal device 10 may include sensors that detect various biological signals, such as a heart rate sensor that detects a heart rate of the user, a brane wave sensor that detects a brain wave of the user, a pulse sensor (pulse wave sensor) that detects a pulse of the user, a respiration sensor (exhalation sensor) that detects respiration of the user, and a perspiration sensor that detects perspiration of the user.

Furthermore, the sensor unit 16 includes a camera (image sensor) that detects an image. For example, the sensor unit 16 includes an image sensor for imaging the user. The sensor unit 16 may include a plurality of cameras (image sensors). For example, the sensor unit 16 may include a first image sensor and a second image sensor. The first image sensor captures a surgical image. The second image sensor images the user. For example, the sensor unit 16 may include a motion sensor.

For example, the sensor unit 16 includes an acceleration sensor. For example, the sensor unit 16 includes a sensor that detects acceleration information of the terminal device 10 at the time when the user performs a predetermined operation. The sensor unit 16 includes a sensor (position sensor) that detects the position of the terminal device 10. For example, the sensor unit 16 may include a global positioning system (GPS) sensor. Furthermore, when the position information of the terminal device 10 is acquired as the sensor information, the sensor unit 16 may acquire the position information of a base station performing communication and the position information of the terminal device 10 estimated by using radio waves of wireless fidelity (WiFi) (registered trademark).

Furthermore, the sensor unit 16 is not limited to the above-described sensors, and may include various sensors. For example, the sensor unit 16 may include a sensor that detects information on the outside of the terminal device 10.

Note that the sensors that detect the above-described various pieces of information in the sensor unit 16 may be a common sensor, or may be implemented by different sensors.

[1-3. Procedure of Information Processing According to Embodiment]

Next, a procedure of the information processing according to the embodiment will be described with reference to FIGS. 4 to 6.

First, a flow of selection processing performed by the information processing apparatus according to the embodiment of the present disclosure will be described with reference to FIG. 4. FIG. 4 is a flowchart illustrating a procedure of the selection processing according to the embodiment of the present disclosure.

Figure 4:
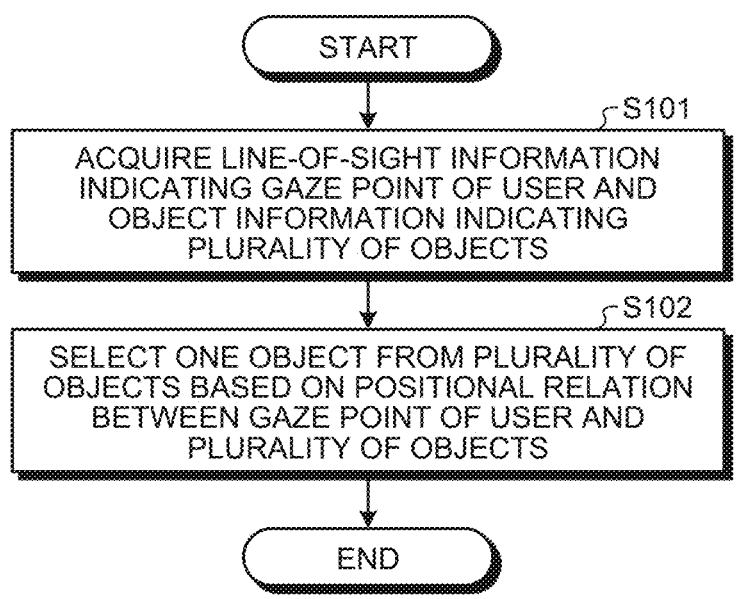
FIG. 4 is a flowchart illustrating a procedure of selection processing according to the embodiment of the present disclosure.

As illustrated in FIG. 4, the information processing apparatus 100 acquires line-of-sight information indicating a gaze point of the user and object information indicating a plurality of objects (Step S101). The information processing apparatus 100 selects one object from a plurality of objects based on the positional relation between the gaze point of the user and the plurality of objects (Step S102).

Next, a flow of processing of determining an area by the information processing apparatus according to the embodiment of the present disclosure selecting a plurality of points will be described with reference to FIG. 5. FIG. 5 is a flowchart illustrating a procedure of determining an area by selecting a plurality of points.

Figure 5:
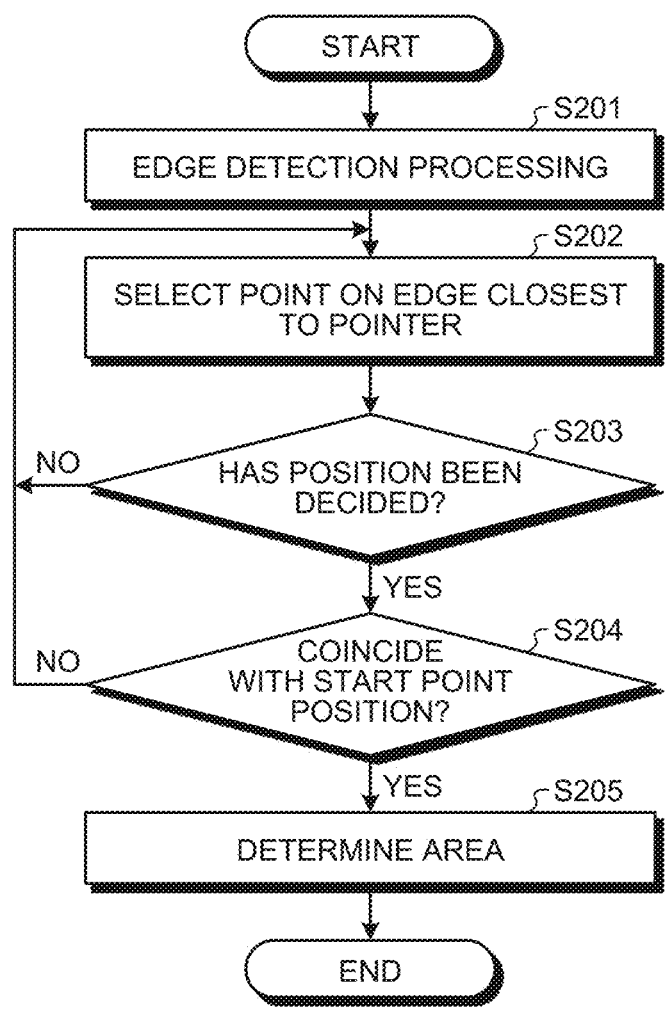
FIG. 5 is a flowchart illustrating a procedure of area determination performed by selecting a plurality of points.

As illustrated in FIG. 5, the information processing apparatus 100 executes edge detection processing (Step S201). For example, the information processing apparatus 100 executes the edge detection processing on a captured surgical image.

Then, the information processing apparatus 100 selects a point on an edge closest to a pointer (point) related to the line of sight of the user (Step S202). For example, the information processing apparatus 100 selects a point on the edge closest to the gaze point of the user. For example, the information processing apparatus 100 may set a gaze point or a position finely adjusted by the head based on the gaze point position as a pointer position.

Then, the information processing apparatus 100 judges whether or not the position has been decided (Step S203). For example, the information processing apparatus 100 judges whether or not the position selected in Step S202 has been decided to be used by the user. When the position has not been decided (Step S203: No), the information processing apparatus 100 returns to Step S202, and repeats the processing.

In contrast, when the position has been decided (Step S203: Yes), the information processing apparatus 100 judges whether or not the position coincides with a start point position (Step S204). For example, when the selected position is decided to be used by the user, the information processing apparatus 100 judges whether or not the position coincides with the start point position, that is, the position first selected in the selection processing. When the decided position does not coincide with the start point position (Step S204: No), the information processing apparatus 100 returns to Step S202 and repeats the processing.

In contrast, when the decided position coincides with the start point position (Step S204: Yes), the information processing apparatus 100 determines an area (Step S205). For example, when the decided position coincides with the start point position, the information processing apparatus 100 determines an area surrounded by the plurality of decided points as a selected area.

Note that, although, in the above-described example, a case where the information processing apparatus 100 selects (generates) an area based on a plurality of points selected based on the gaze point of the user has been described in one example, the information processing apparatus 100 may select an area based on the gaze point of the user. This point will be described with reference to FIG. 6. FIG. 6 is a flowchart illustrating a procedure of selection of an area according to the embodiment of the present disclosure. For example, FIG. 6 illustrates a flow of area selection processing performed by the information processing apparatus according to the embodiment of the present disclosure.

Figure 6:
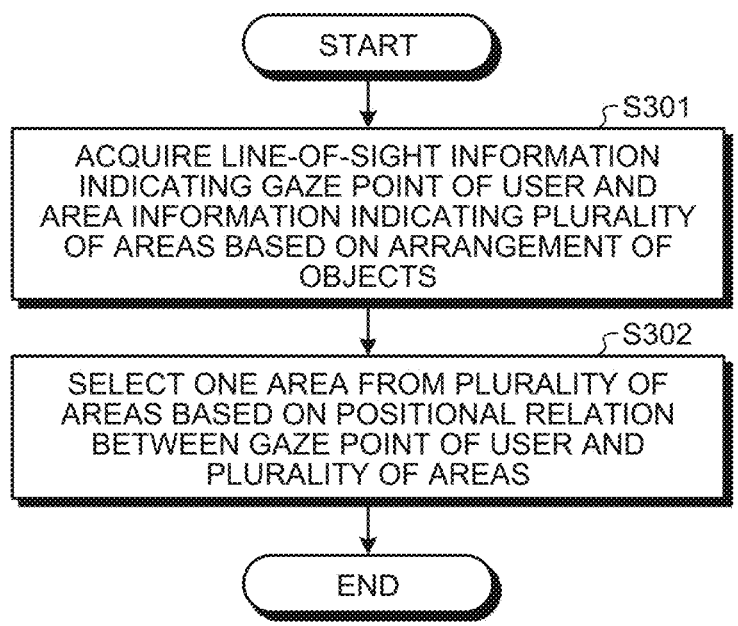
FIG. 6 is a flowchart illustrating a procedure of selection of an area according to the embodiment of the present disclosure.

As illustrated in FIG. 6, the information processing apparatus 100 acquires line-of-sight information indicating a gaze point of the user and area information indicating a plurality of areas based on the arrangement of objects (Step S301). The information processing apparatus 100 selects one area from a plurality of areas based on the positional relation between the gaze point of the user and the plurality of areas (Step S302).

[1-4. Processing Example]

One example of various pieces of processing will now be described with reference to FIGS. 7 to 15. Note that description of points similar to those in FIG. 1 will be appropriately omitted.

[1-4-1. Area Selection Example]

Figure 7:
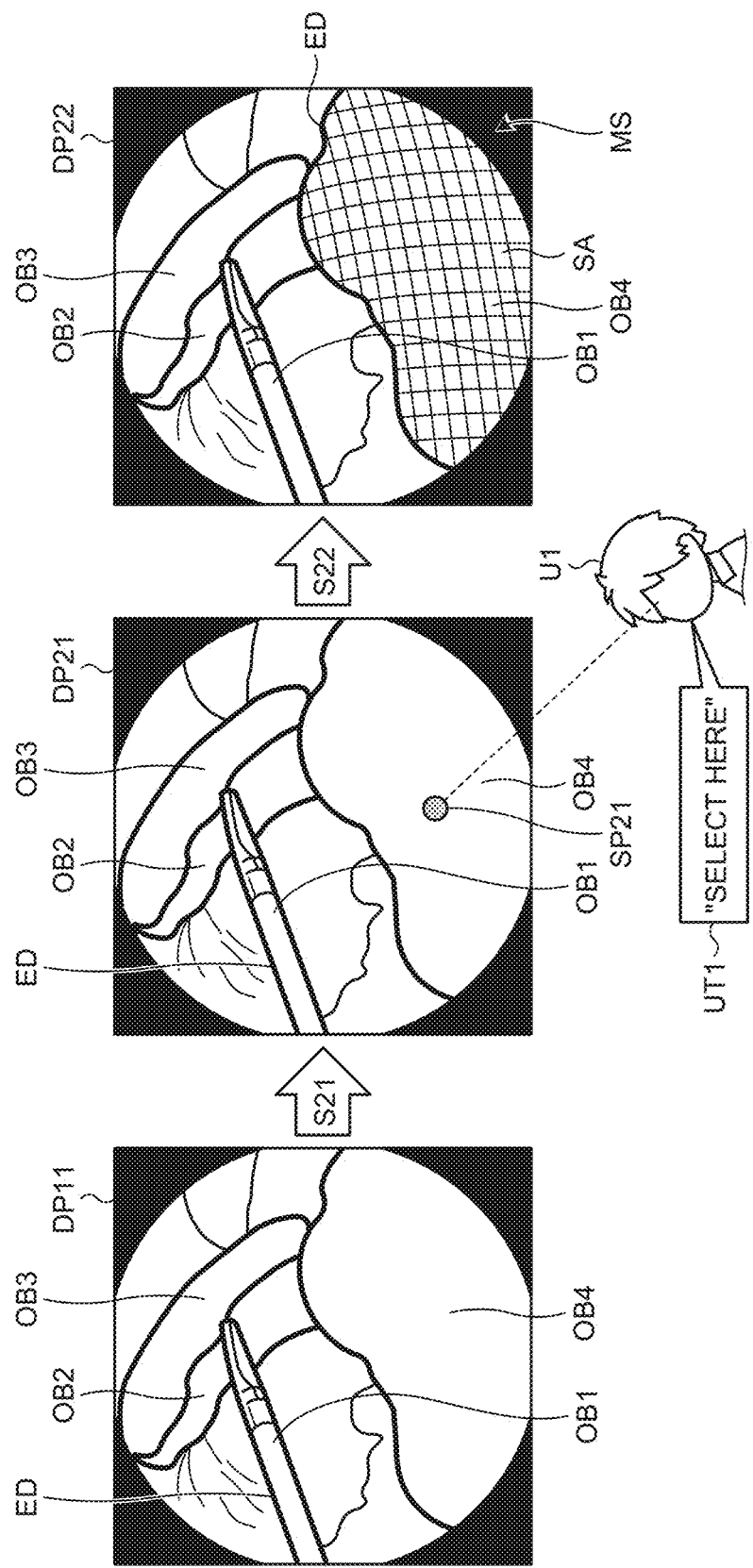
FIG. 7 illustrates one example of area selection processing.

First, area selection corresponding to the processing flow in FIG. 6 will be described with reference to FIG. 7. FIG. 7 illustrates one example of area selection processing.

In the example of FIG. 7, the information processing apparatus 100 detects boundaries ED (e.g., corresponding to thick line portions in image DP11) as illustrated in the image DP11 by performing edge detection. Since this point is similar to that in the image DP11 in FIG. 1, description thereof will be omitted.

The information processing apparatus 100 selects one area from a plurality of areas based on the positional relation between the gaze point of the user U1 and the plurality of areas (Step S21). For example, the information processing apparatus 100 selects, as one area (also referred to as "selected area"), an area where the gaze point of the user U1 is located from a plurality of areas formed by the boundaries ED that separate the plurality of objects OB1 to OB4.

For example, the information processing apparatus 100 selects, as a selected area, an area where the gaze point of the user U1 is located from a plurality of areas such as an area corresponding to each object such as the plurality of objects OB1 to OB4. In the example of FIG. 7, as illustrated in an image DP21, a gaze point SP21 of the user U1 is located in an area corresponding to the object OB4, so that the information processing apparatus 100 selects the area corresponding to the object OB4 as a selected area. That is, the information processing apparatus 100 selects, as a selected area, an area which corresponds to the object OB4 and is formed by the boundary ED. The object OB4 is a part of an organ. In this manner, the information processing apparatus 100 can flexibly select a target in accordance with a line of sight of the user.

The user U1 confirms that the area corresponding to the object OB4 has been selected. Then, the user U1 performs an operation (determination operation) for determining (deciding) the area as a selected area. For example, as illustrated in an image DP21, the user U1 performs a determination operation of setting the area corresponding to the object OB4 as a selected area that has been determined (also referred to as "determined selected area") by issuing an utterance UT1 such as "select here" with the gaze point SP21 being located in the area corresponding to the object OB4. In this case, the information processing apparatus 100 determines (decides) the area corresponding to the object OB4 as a selected area (determined selected area) in response to detection of the utterance UT1 of the user U1. In this manner, the user U1 issues an utterance while looking at a candidate of an area desired to be meshed. This causes the information processing apparatus 100 to select the area corresponding to the object OB4 as an area to be processed in relation to editing.

Then, the information processing apparatus 100 generates a mesh that divides the selected area into a plurality of partial areas (Step S22). In the example of FIG. 7, the information processing apparatus 100 generates a mesh MS that divides the area corresponding to the object OB4 into a plurality of partial areas SA. For example, the information processing apparatus 100 generates the mesh MS that divides the area corresponding to the object OB4 into a plurality of partial areas SA having a rectangular shape. Then, as illustrated in an image DP22, the information processing apparatus 100 superimposes and displays the generated mesh MS on the area corresponding to the object OB4. Note that, since the generation and superimposed display of the mesh is performed by using a known technique related to the mesh, detailed description thereof will be omitted.

As described above, the information processing apparatus 100 meshes an area having a gaze point if the area is closed space. This enables the information processing apparatus 100 to select any area and perform desired editing such as filling with the mesh MS. Note that the mesh MS in a screen DP22 of FIG. 7 is merely one example, and the size or style of the mesh MS may be changed to any form.

For example, the information processing apparatus 100 may allow the user to designate the size or style of the mesh MS by a speech. In this case, when the user U1 utters "coarse mesh", the information processing apparatus 100 changes the style of the mesh MS to a coarse form. Furthermore, when the user U1 utters "fine mesh", the information processing apparatus 100 changes the style of the mesh MS to a fine form. Furthermore, when the user U1 utters "triangular mesh", the information processing apparatus 100 changes the shape of the partial areas SA of the mesh MS from rectangles (quadrangle) to triangles. Furthermore, for example, the information processing apparatus 100 may generate the mesh so as to follow a three-dimensional shape of the object by a method such as depth measurement and machine learning.

Note that the information processing apparatus 100 may use the area selection processing described with reference to FIGS. 6 and 7 and processing of selecting a point (also referred to as "point selection") in FIG. 1 in combination, or may switch between a mode of the area selection processing and a mode of point selection processing to execute the modes.

For example, the information processing apparatus 100 may operate in the point selection mode described with reference to FIG. 1 when operating in the above-described free pointing, and may operate in the area selection mode described with reference to FIGS. 6 and 7 when operating in the above-described free pointing. Note that the above is merely one example, and the information processing apparatus 100 may operate while appropriately switching between the mode of the area selection processing and the mode of the point selection processing by using various pieces of information such as designation of the user as long as the information processing apparatus 100 can perform a desired operation.

[1-4-2. Example of Selection Made by Designating Range]

Figure 8:
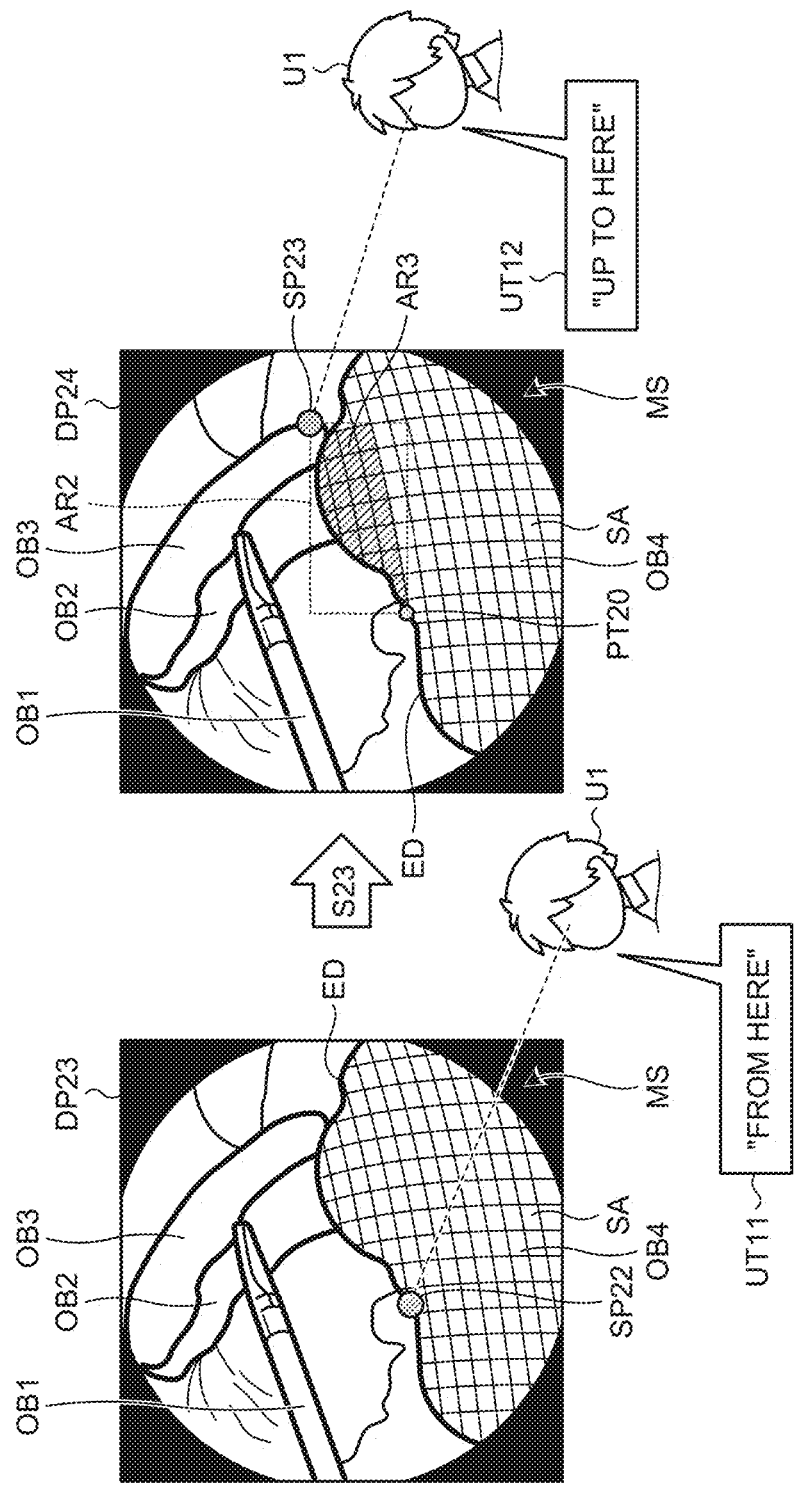
FIG. 8 illustrates one example of processing of selection made by designating a range.

Note that the information processing apparatus 100 may designate an area by selecting two points with a speech and a line of sight or the head direction. In this regard, selection using the area selected in FIG. 7 will be described with reference to FIG. 8. FIG. 8 illustrates one example of processing of selection made by designating a range. Note that description of points similar to those in FIG. 7 will be appropriately omitted.

An image DP23 of FIG. 8 is obtained by indicating a gaze point SP22 of the user U1 in the image DP22 of FIG. 7. The user U1 confirms that a point at the position of the gaze point SP22 has been selected. Then, the user U1 performs an operation for determining (deciding) a point PT20 at the position of the gaze point SP22 as a first point (determination operation). For example, the user U1 performs the determination operation of setting the point PT20 at the position of the gaze point SP22 as the determined first point by issuing an utterance UT11 such as "from here". In this case, the information processing apparatus 100 determines (decides) the point PT20 at the position of the gaze point SP22 as the first point in response to detection of the utterance UT11 of the user U1.

Thereafter, the user U1 changes the line of sight to select another point. An image DP24 of FIG. 8 indicates the position of a gaze point SP23 of the user U1 after the line of sight of the user U1 is changed. The user U1 confirms that a point at the position of the gaze point SP23 has been selected. Then, the user U1 performs an operation for determining (deciding) a point at the position of the gaze point SP23 as a second point (determination operation). For example, the user U1 performs the determination operation of setting the point at the position of the gaze point SP23 as the determined second point by issuing an utterance UT12 such as "up to here". In this case, the information processing apparatus 100 determines (decides) the point at the position of the gaze point SP23 as the second point in response to detection of the utterance UT12 of the user U1.

The information processing apparatus 100 has determined the first point and the second point. Then, the information processing apparatus 100 selects only a portion corresponding to the mesh MS in a rectangular area having a line connecting the first point and the second point as a diagonal line (Step S23). In the example of FIG. 8, as illustrated in image DP24, the information processing apparatus 100 selects only a portion overlapping the rectangular area (dotted rectangle) having a line connecting the point PT20, which is the first point, and a point at the position of the gaze point SP23, which is the second point, as a diagonal line from the plurality of partial areas SA in the mesh MS. Note that, in the example of FIG. 8, an example is illustrated in which only a portion completely overlapping the rectangular area (dotted rectangle) having a line connecting the point PT20, which is the first point, and a point at the position of the gaze point SP23, which is the second point, as a diagonal line from the plurality of partial areas SA in the mesh MS. Note that the information processing apparatus 100 may select a portion at least a part of which overlaps the rectangular area (dotted rectangle) having a line connecting the point PT20, which is the first point, and a point at the position of the gaze point SP23, which is the second point, as a diagonal line from the plurality of partial areas SA in the mesh MS.

As described above, the information processing apparatus 100 selects only an area AR3, which is a part of the mesh MS, in the rectangular area having a line connecting two points of the point PT20 and the point at the position of the gaze point SP23 as a diagonal line. This causes the information processing apparatus 100 to select only a portion overlapping a rectangular area having a line connecting optional two points as a diagonal line from the plurality of partial areas SA of the mesh MS.

[1-4-3. Example of Continuously Selecting Partial Areas]

Figure 9:
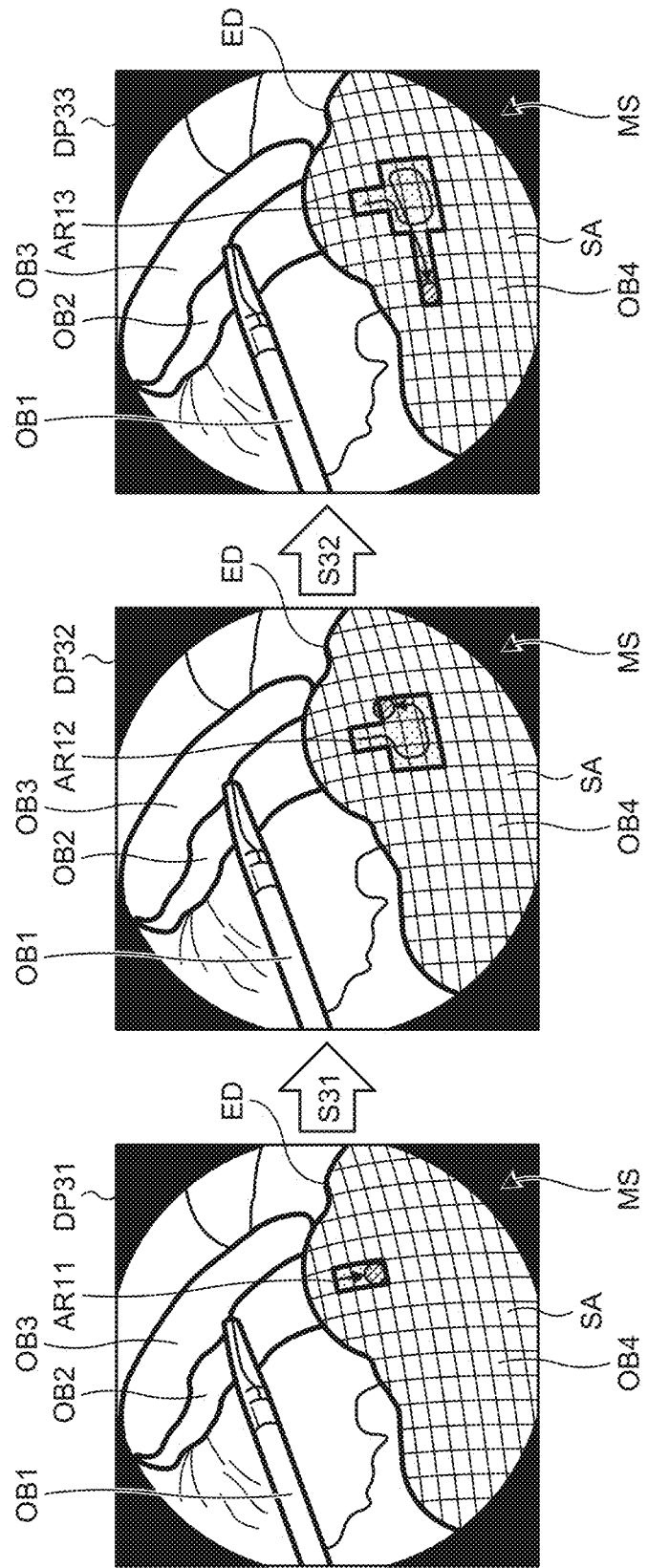
FIG. 9 illustrates one example of processing of continuously selecting partial areas.

Note that partial area selection is not limited to the processing in FIG. 8, but may be various pieces of processing. For example, the information processing apparatus 100 may continuously select tracks based on the gaze point and the head direction. This point will be described with reference to FIG. 9. FIG. 9 illustrates one example of processing of continuously selecting partial areas. Note that, although a case where an area is selected in response to a change in the position of the gaze point will be described below, the area may be described in response to a change in the position or posture of the head.

As illustrated in an image DP31, the information processing apparatus 100 selects an area in response to a change in the position of the gaze point of the user U1. For example, the user U1 may change the position of the line of sight (gaze point) by moving only the eyes, or may change the position of the line of sight (gaze point) by changing the position or posture of the head. For example, the user U1 may change the line of sight (gaze point) by continuously adjusting the position in a head direction. This causes the information processing apparatus 100 to select an area AR11 as illustrated in the image DP31.

Then, the information processing apparatus 100 selects an area in response to a change in the position of the gaze point of the user U1 (Step S31). In the example of FIG. 9, the information processing apparatus 100 selects an area AR12 as illustrated in an image DP32. That is, the information processing apparatus 100 enlarges the selected area from the area AR11 to the area AR12.

Furthermore, the information processing apparatus 100 selects an area in response to a change in the position of the gaze point of the user U1 (Step S32). In the example of FIG. 9, the information processing apparatus 100 selects an area AR13 as illustrated in an image DP33. That is, the information processing apparatus 100 enlarges the selected area from the area AR12 to the area AR13.

As described above, the information processing apparatus 100 continuously expands and adjusts the area in response to a change in the position of the gaze point of the user. For example, when a line of sight is used, the information processing apparatus 100 does not need to make a drawing for a certain period of time in a case where the gaze point temporarily goes out of the mesh. Furthermore, the information processing apparatus 100 may be allowed to draw any figure by changing the mesh size.

[1-4-4. Example of Change in Selection Width]

Figure 10:
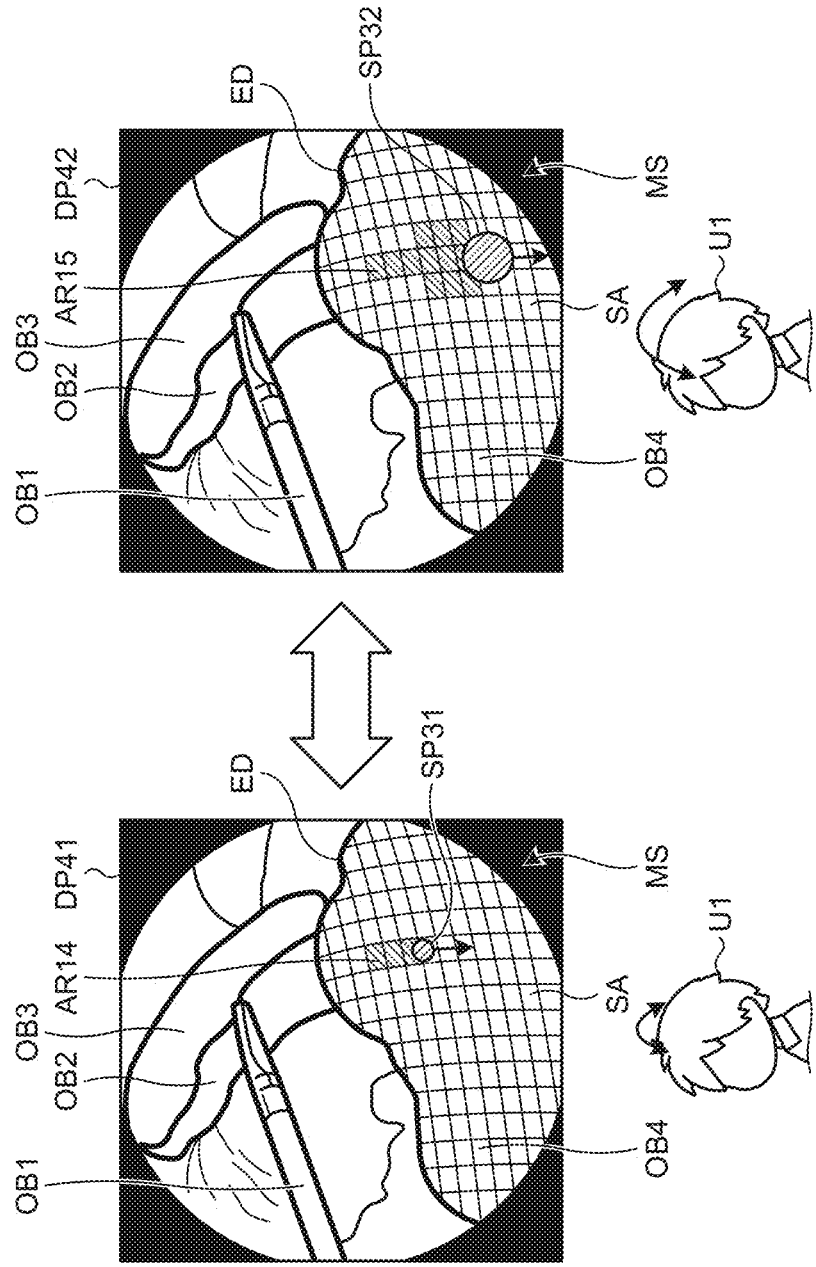
FIG. 10 illustrates one example of a change in a selection width.

Furthermore, a selection width may be appropriately changed. This point will be described with reference to FIG. 10. FIG. 10 illustrates one example of a change in the selection width.

For example, the information processing apparatus 100 may adjust a brush thickness in accordance with the inclination of the head of the user U1. The information processing apparatus 100 may increase a selection width (e.g., brush size) for selecting an area as the inclination of the head of the user U1 increases.

An image DP41 of FIG. 10 indicates a state of a small selection width. In this case, the information processing apparatus 100 selects an area corresponding to a gaze point SP31 having a small size. For example, the information processing apparatus 100 selects a partial area SA having a small size, through which a gaze point SP31 passes, such as an area AR14 from the plurality of partial areas SA of the mesh MS.

Furthermore, an image DP42 of FIG. 10 indicates a state of a large selection width. In this case, the information processing apparatus 100 selects an area corresponding to a gaze point SP32 having a large size. For example, the information processing apparatus 100 selects a partial area SA having a small size, through which a gaze point SP32 passes, such as an area AR15 from the plurality of partial areas SA of the mesh MS.

Note that the information processing apparatus 100 may decrease the size of the selection width in accordance with the inclination of the head of the user U1. In this manner, the information processing apparatus 100 increases or decreases the selection width in accordance with the inclination of the head of the user U1. This enables the information processing apparatus 100 to set any selection width and select an area.

Furthermore, as described above, a subject may move or a viewpoint of a camera may move during selection operation. In such a case, in order that an unintended area is not filled (not selected), the information processing apparatus 100 may maintain a state in which the mesh is fixed on a screen so that the filling position (selected position) does not shift on the screen. For example, the information processing apparatus 100 may use an existing method of performing feature point matching processing between video frames and causing following as a method for performing such processing.

[1-4-5. Editing Example]

Furthermore, an area generated by selecting a plurality of points may be appropriately edited. This point will be described with reference to FIGS. 11 and 12.

[1-4-5-1. Change of Selected Point]

Figure 11:
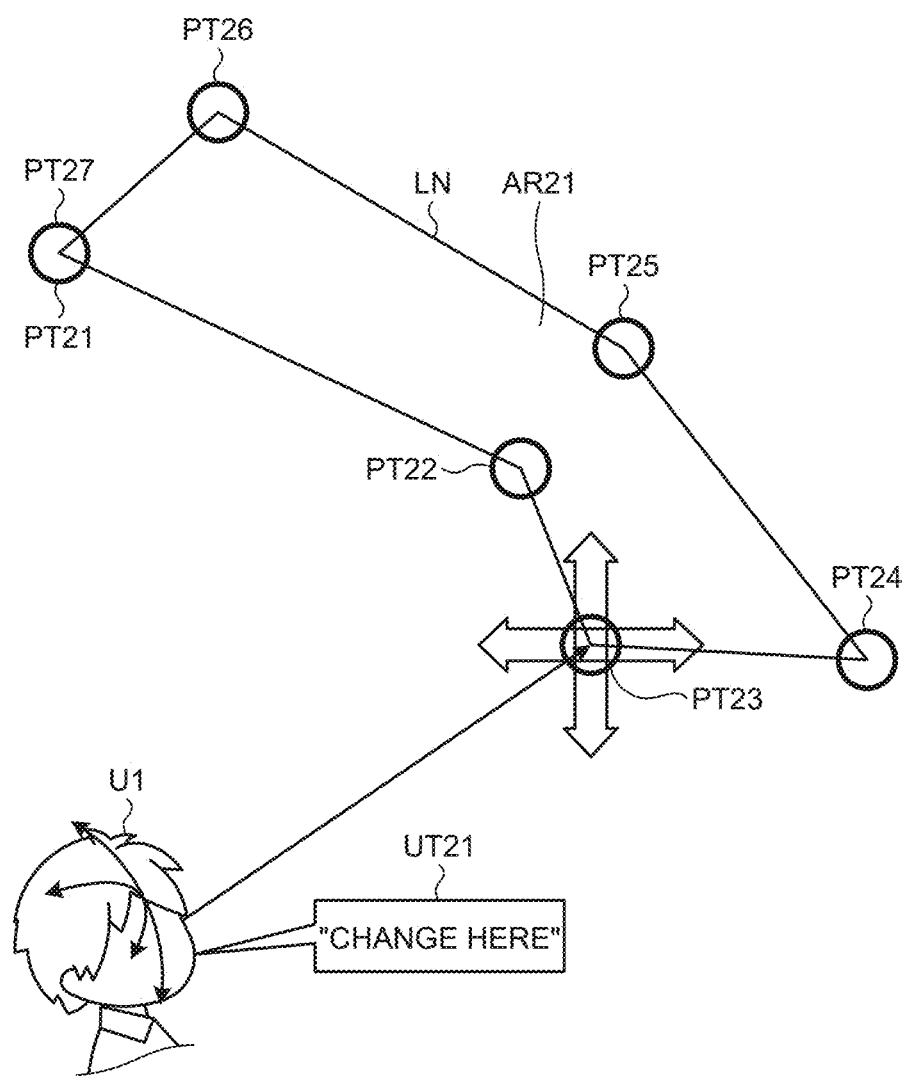
FIG. 11 illustrates one example of editing performed by changing a point.

First, editing of an area performed by adjusting the positions of the selected points will be described with reference to FIG. 11 in one example of change of a point. FIG. 11 illustrates one example of editing performed by changing a point. Note that the change of a point is not limited to the adjustment (change) of the positions of the selected points, and may be, for example, deletion of the positions of the selected points.

In the example of FIG. 11, a case where seven points PT21 to PT27 are determined (decided) as determined selected points is illustrated. For example, the information processing apparatus 100 selects the seven points in the order of points PT21, PT22, PT23, PT24, PT25, PT26, and PT27, and connects the points in the order with the line LN to generate an area AR21. That is, the information processing apparatus 100 generates the area AR21 having, as a boundary, the line LN connecting the plurality of points PT21 to PT27. The point PT21 serves as a start point. The point PT27 serves as an end point. For example, the plurality of points PT21 to PT27 are designated when an area is set.

Then, the information processing apparatus 100 selects a point to be changed from the plurality of points PT21 to PT27 in accordance with the line of sight of the user U1. For example, the information processing apparatus 100 selects a point overlapping the position of the gaze point of the user U1 as the point to be changed. In FIG. 11, the information processing apparatus 100 selects the point PT23 corresponding to the position of the gaze point of the user U1 as the point to be changed. In this manner, the information processing apparatus 100 selects a target with a line of sight.

For example, the user U1 selects the point PT23 as the point to be changed by issuing an utterance UT21 such as "select here" with the gaze point overlapping the point PT23. The information processing apparatus 100 selects the point PT23 as the point to be changed in response to the utterance UT21 of the user U1.

Then, for example, when the position of the point PT23 is desired to be moved, the user U1 changes the position of the gaze point. The information processing apparatus 100 moves the position of the point PT23 following the change in the position of the gaze point of the user U1. Note that the user U1 may change the position of the line of sight (gaze point) by moving only his/her eyes, or may change the position of the line of sight (gaze point) by changing the position or posture of his/her head. In this manner, the information processing apparatus 100 may continuously adjust the position (of the point) in the head direction.

Furthermore, when the point PT23 is desired to be deleted, the user U1 utters "delete this" with the point PT23 being selected as the point to be changed. When detecting the utterance such as "delete this" of the user U1 with the point PT23 being selected as the point to be changed, the information processing apparatus 100 deletes the point PT23. In this case, the information processing apparatus 100 excludes the point PT23 from the plurality of points PT21 to PT27. Then, the information processing apparatus 100 updates the area AR21 to a shape in which the line LN connects six points of the points PT21, PT22, PT24, PT25, PT26, and PT27 in this order.

[1-4-5-2. Addition of Point]

Figure 12:
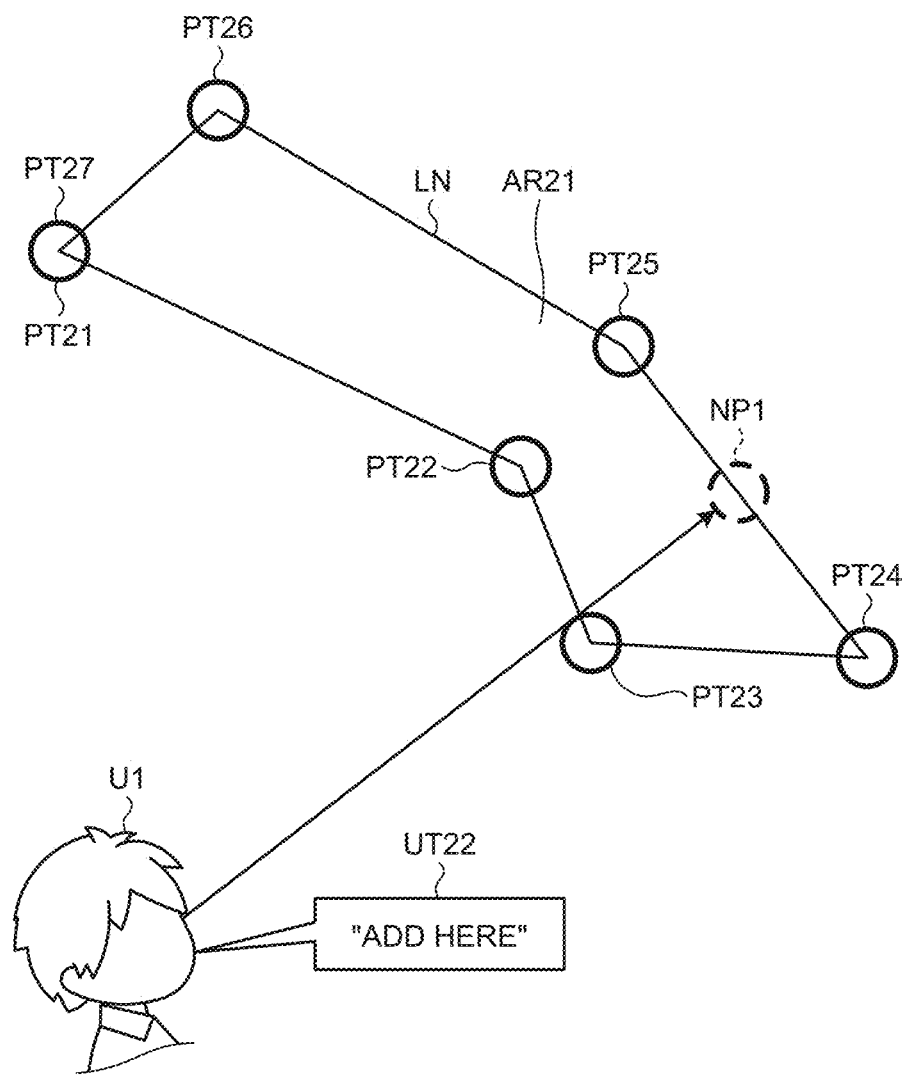
FIG. 12 illustrates one example of the editing performed by adding a point.

Next, editing of an area performed by adding a new point will be described with reference to FIG. 12. FIG. 12 illustrates one example of the editing performed by adding a point. Specifically, FIG. 12 illustrates one example of the editing performed by adding a new point. Note that description of points similar to those in FIG. 11 will be omitted.

The user U1 selects a position to which a point is desired to be newly added with a line of sight. For example, the user U1 selects a position to which a point is desired to be newly added on the line LN with a line of sight. The line LN is a boundary forming the area AR21. In the example of FIG. 12, the user U1 desires to add a new point between the point PT24 and the point PT25. Note that, when the gaze point of the user U1 does not overlap the line L, the information processing apparatus 100 may select a position (point) closest to the gaze point of the user U1 on the line LN.

In this case, the information processing apparatus 100 newly adds a point NP1 on the line LN in accordance with the line of sight of the user U1. In FIG. 12, the information processing apparatus 100 adds the point NP1 to the position of the gaze point of the user U1. In this case, the information processing apparatus 100 generates the area AR21 having, as a boundary, the line LN connecting the plurality of points PT21, PT22, PT23, PT24, NP1, PT25, PT26, and PT27 in this order. The user U1 may change the shape of the area AR21 by changing the position of the newly added point NP1 by an operation as illustrated in FIG. 11.

[1-4-6. Multiple Layer Example]

Furthermore, the information processing apparatus 100 may perform the selection processing by using not only one layer (image) but a plurality of layers (images). This point will be described with reference to FIGS. 13 to 15.

[1-4-6-1. Selection Example 1 (Medical Image)]

Figure 13:
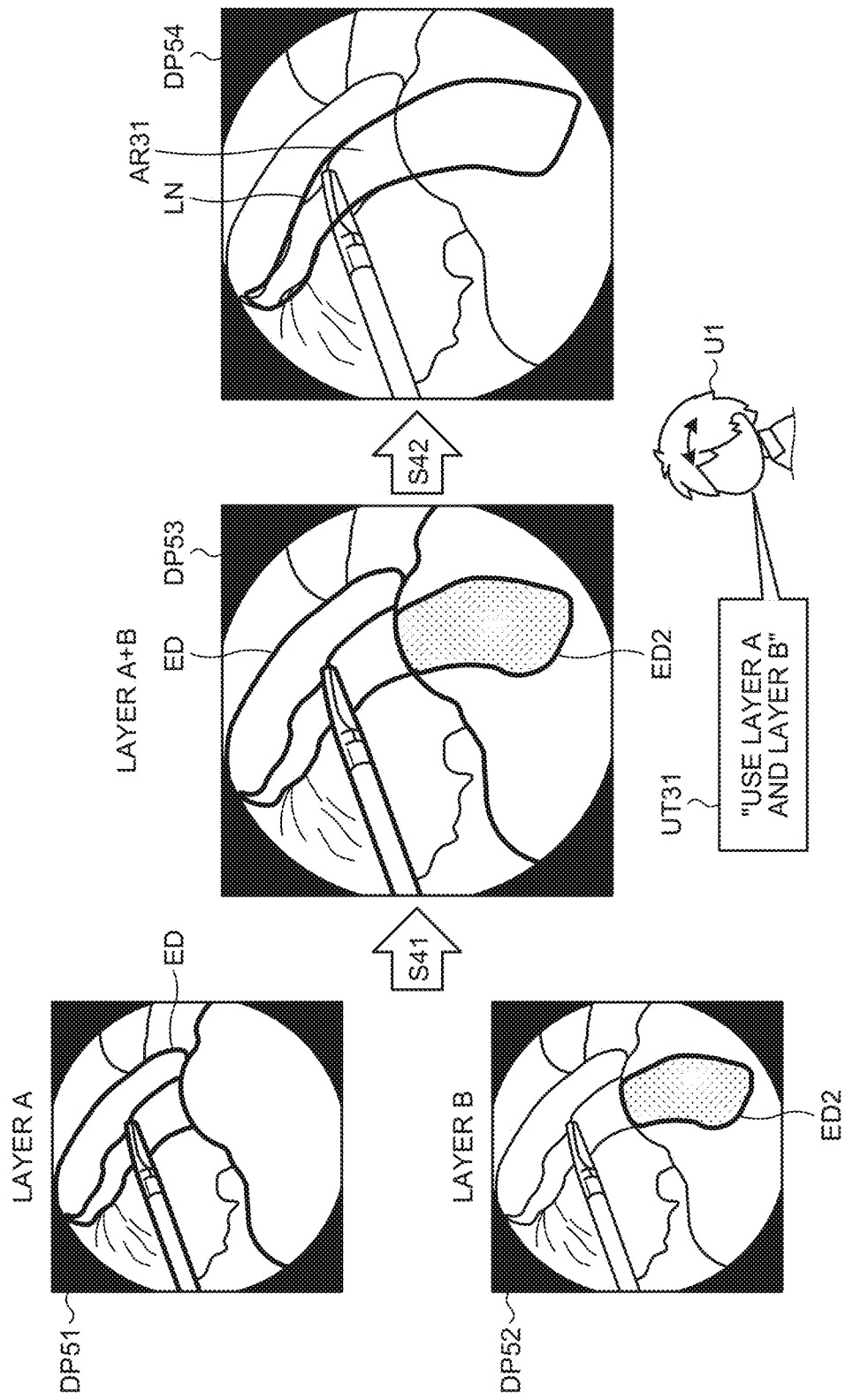
FIG. 13 illustrates one example of selection using a plurality of layers.

First, selection processing using a plurality of layers of selected points in a case of targeting a medical image will be described with reference to FIG. 13. FIG. 13 illustrates one example of selection using a plurality of layers.

An image DP51 of FIG. 13 indicates an image corresponding to a layer A, and is an image (layer) including information on the boundary ED detected by edge detection similarly to that in FIG. 1. Furthermore, an image DP52 of FIG. 13 indicates an image corresponding to a layer B, and is an image (layer) including information on a target (organ) in a place hidden behind, for example, a part of another target (organ). In the example of FIG. 13, the image DP52 includes a boundary ED2 indicating an edge of the target hidden behind, for example, a part of another target (organ). For example, the image DP52 may be three-dimensional (3D) information generated from, for example, computed tomography (CT) scan data.

As illustrated in an image DP53, the information processing apparatus 100 generates information in which information on the layer A and information on the layer B are overlapped (Step S41). The information processing apparatus 100 may display the image DP53 indicating the information on the layer A and the information on the layer B. Then, the information processing apparatus 100 may receive selection of the user U1 with both the information on the layer A (e.g., boundary ED) and the information on the layer B (e.g., boundary ED2) as selection targets.

For example, the user U1 may set both the information on the layer A (e.g., boundary ED) and the information on the layer B (e.g., boundary ED2) as selection targets by issuing an utterance UT31 such as "use the layer A and the layer B". In this case, the information processing apparatus 100 receives selection of the user U1 with both the information on the layer A (e.g., boundary ED) and the information on the layer B (e.g., boundary ED2) as selection targets in response to detection of the utterance UT31 of the user U1. For example, the information processing apparatus 100 may use OR (logical sum) of the layer A and the layer B as edge information (boundary information). Then, the information processing apparatus 100 may display the edge information (boundary information) of the logical sum of the layer A and the layer B.

Furthermore, the information processing apparatus 100 may switch between pieces of information on a layer to be selected in accordance with designation of the user U1. For example, when the user U1 issues an utterance for designating switching to a single layer, such as "only the layer B", the information processing apparatus 100 may set only information on one layer as a selection target of the user U1. Note that the information processing apparatus 100 may designate a layer in a depth direction by changing the head of the user U1 back and forth. In this case, the information processing apparatus 100 may set a back layer (e.g., layer B) as a selection target when the user U1 puts his/her head forward, and may set a front layer (e.g., layer A) as a selection target when the user U1 pulls his/her head back. In this manner, the information processing apparatus 100 may switch between layers to be selected in response to a change in the position or posture of the head of the user U1.

When detecting the utterance of "only the layer B" of the user U1, the information processing apparatus 100 receives selection of the user U1 with both the information on the layer B (e.g., boundary ED2) as a selection target. In this case, the information processing apparatus 100 may display only the information on the layer B (i.e., image DP52), or may display both the information on the layer A (e.g., boundary ED) and the information on the layer B (e.g., boundary ED2) (i.e., image DP53). In this manner, the user U1 selects a desired target by selecting a point and an area while designating a selection target from a plurality of layers.

In the example of FIG. 13, the information processing apparatus 100 selects a plurality of points including a point on the boundary ED2 of a target hidden behind, for example, a part of another target (organ) by the user U1 performing selection using information on the boundary ED2 of the layer B. This causes the information processing apparatus 100 to generate an area AR31 having, as a boundary, the line LN connecting a plurality of points selected by the user U1 by using a plurality of layers as illustrated in an image DP54 (Step S42).

In this manner, in the example of FIG. 13, the information processing apparatus 100 can designate an area by superimposing information layers in the depth direction. That is, the information processing apparatus 100 can select an area including a back portion by using a plurality of pieces of layer information.

Note that the information processing apparatus 100 may use edge information (boundary information) detected by each algorithm of edge detection such as an algorithm of edge detection, segmentation detection, depth map, or the like as one layer. For example, the information processing apparatus 100 may use edge information (boundary information) detected by edge detection as a first layer (e.g., layer A), and may use edge information (boundary information) detected by segmentation detection as a second layer.

[1-4-6-2. Selection Example 2 (Map)]

Note that the above-described selection performed by switching between a plurality of layers may be applied not only to a surgical image but to various pieces of information. This point will be simply described with reference to FIGS. 14 and 15. Note that description of points similar to those in FIG. 13 will be omitted.

Figure 14:
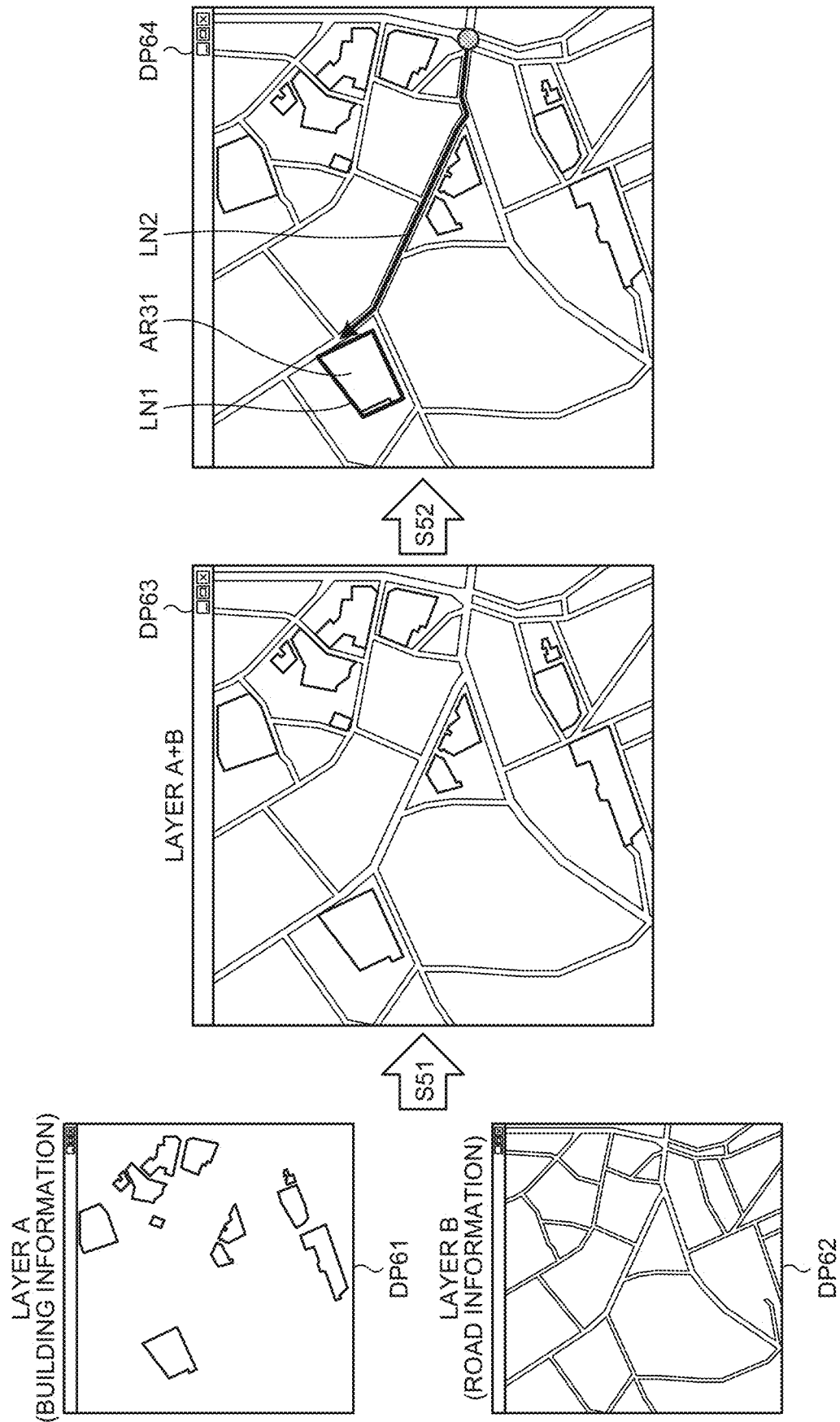
FIG. 14 illustrates one example of the selection using a plurality of layers.

First, selection processing using a plurality of layers of selected points in a case of targeting a map will be described with reference to FIG. 14. FIG. 14 illustrates one example of selection using a plurality of layers.

An image DP61 of FIG. 14 indicates an image corresponding to the layer A, and is an image (layer) including building information in the map information. For example, the image DP61 includes information on an edge (boundary) of a building in the map information.

Furthermore, an image DP62 of FIG. 14 indicates an image corresponding to the layer B, and is an image (layer) including road information in the map information. For example, the image DP62 includes road information in the map information.

As illustrated in an image DP63, the information processing apparatus 100 generates information in which information on the layer A and information on the layer B are overlapped (Step S51). The information processing apparatus 100 may display the image DP63 indicating the information on the layer A and the information on the layer B. Then, the information processing apparatus 100 may receive selection of the user U1 with both the information on the layer A (e.g., edge of building) and the information on the layer B (e.g., road) as selection targets.

In the example of FIG. 14, the information processing apparatus 100 selects an area of a building by the user U1 performing selection using information on a boundary of the building of the layer A, and selects a road by the user U1 performing selection using information on a road of the layer B. This causes the information processing apparatus 100 to generate the area AR31 formed by a line LN1 connecting points selected by the information on the layer A and a line LN2 connecting points selected by the information on the layer B as illustrated in an image DP64 (Step S52). Note that the line LN2 may be obtained by connecting a plurality of selected points in a selected order, or may be a road (line) corresponding to the selected points.

In this manner, in the example of FIG. 14, the information processing apparatus 100 can perform selection targeting at a plurality of layers whose targeted types are different in pieces of map information. Specifically, the information processing apparatus 100 can surround (select) a building by using the information on the layer A, and draw (select) a route by using the information on the layer B. That is, the information processing apparatus 100 can perform selection targeting at a map by using a plurality of pieces of layer information.

[1-4-6-3. Selection Example 3 (Article)]

Figure 15:
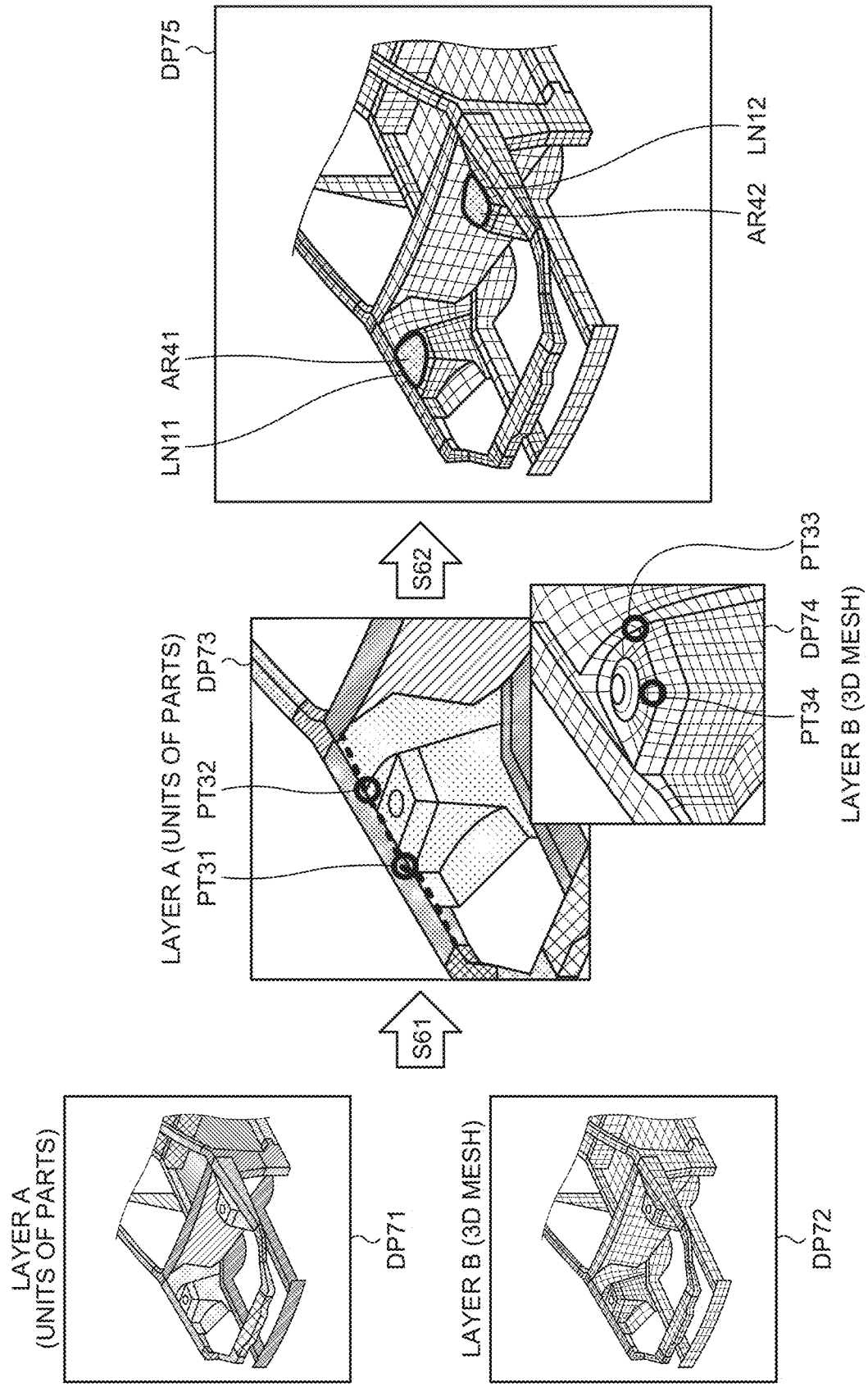
FIG. 15 illustrates one example of the selection using a plurality of layers.

Next, selection processing using a plurality of layers of selected points in a case of targeting an article will be described with reference to FIG. 15. FIG. 15 illustrates one example of selection using a plurality of layers. Specifically, FIG. 15 illustrates one example of selection using a plurality of layers for a vehicle. For example, FIG. 15 illustrates one example of a case where an intended location is selected by a 3D modeling app. Note that the selection may be performed not only for a vehicle but for a structure (real estate) including a house or various articles including an article other than a real estate, such as clothes.

An image DP71 of FIG. 15 indicates an image corresponding to the layer A, and is an image (layer) including information on a body of a vehicle in units of parts (part information). Furthermore, an image DP72 of FIG. 15 indicates an image corresponding to the layer B, and is an image (layer) including information on a 3D mesh of the body of the vehicle. Note that, although, in the images DP71 and DP72 and an image DP75 of FIG. 15, only a portion necessary for description, that is, a front portion of the vehicle body is illustrated, the images DP71, DP72, and DP75 include information on the entire vehicle body.

As illustrated in an image DP73 and an image DP74, the information processing apparatus 100 switches between the information on the layer A and the information on the layer B, and displays the pieces of information (Step S61). Then, the information processing apparatus 100 may receive selection of the user U1 with the displayed layer information among the information on the layer A (e.g., edge of part of vehicle body) and the information on the layer B (e.g., 3D mesh of vehicle body) as a selection target. In this manner, in the example of FIG. 15, the information processing apparatus 100 causes the user U1 to select a point or an area while switching between the information on the layer A and the information on the layer B.

For example, the information processing apparatus 100 selects a point PT31 and a point PT32 by the user U1 performing selection using information in units of parts of the vehicle body of the layer A. The user U1 can easily select the boundary between the parts of the vehicle body by using the layer A.

Furthermore, for example, the information processing apparatus 100 selects a point PT33 and a point PT34 by the user U1 performing selection using information in the 3D mesh of the vehicle body of the layer B. The user U1 can select a detailed position of the vehicle body by using the layer B. This causes the information processing apparatus 100 to generate an area by using points selected by using pieces of information of the information on the layer A and the information on the layer B (Step S62). In the example of FIG. 15, as illustrated in an image DP75, the information processing apparatus 100 generates an area AR41 formed by a line LN11 connecting points (e.g., points PT31 to PT34) selected by using the pieces of information of the information on the layer A and the information on the layer B. Furthermore, as illustrated in the image DP75, the information processing apparatus 100 generates an area AR42 formed by a line LN12 connecting points selected by using the pieces of information of the information on the layer A and the information on the layer B.

In this manner, in the example of FIG. 15, the information processing apparatus 100 can perform selection targeting at a plurality of layers whose types are different even with the same vehicle body information. Specifically, the information processing apparatus 100 can cause the user U1 to select a boundary between parts with the information on the layer A, and cause the user U1 to select the detailed position of the vehicle body with the information on the layer B. That is, the information processing apparatus 100 can perform selection targeting at an article such as a vehicle body by using a plurality of pieces of layer information. This enables the information processing apparatus 100 to select a complicated curved surface portion.

2. Other Embodiments

The processing according to the above-described embodiment may be carried out in various different forms (variations) other than the above-described embodiment. For example, the system configuration is not limited to that in the above-described example, and may be carried out in various modes. This point will be described below. Note that description of points similar to those of the information processing apparatus 100 according to the embodiment will be appropriately omitted.

[2-1. Variation]

Figure 16:
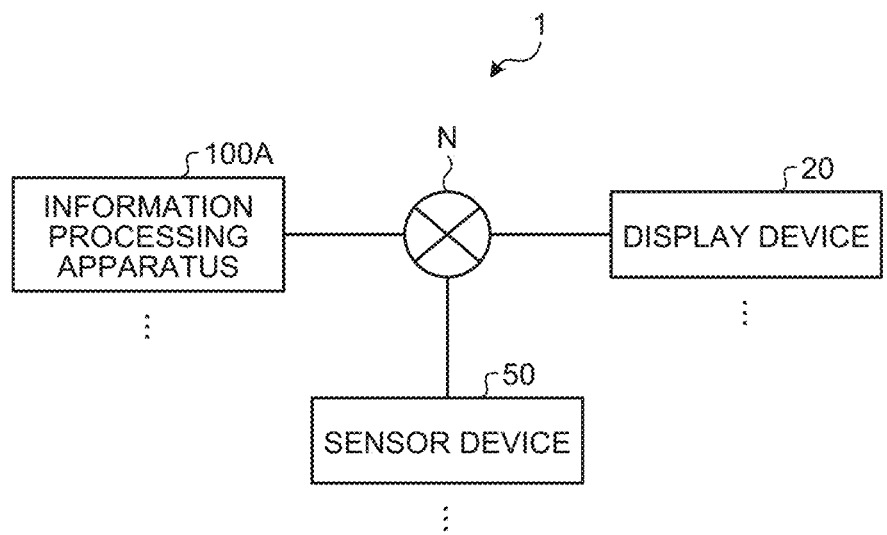
FIG. 16 illustrates a configuration example of an information processing system according to a variation of the present disclosure.
Figure 17:
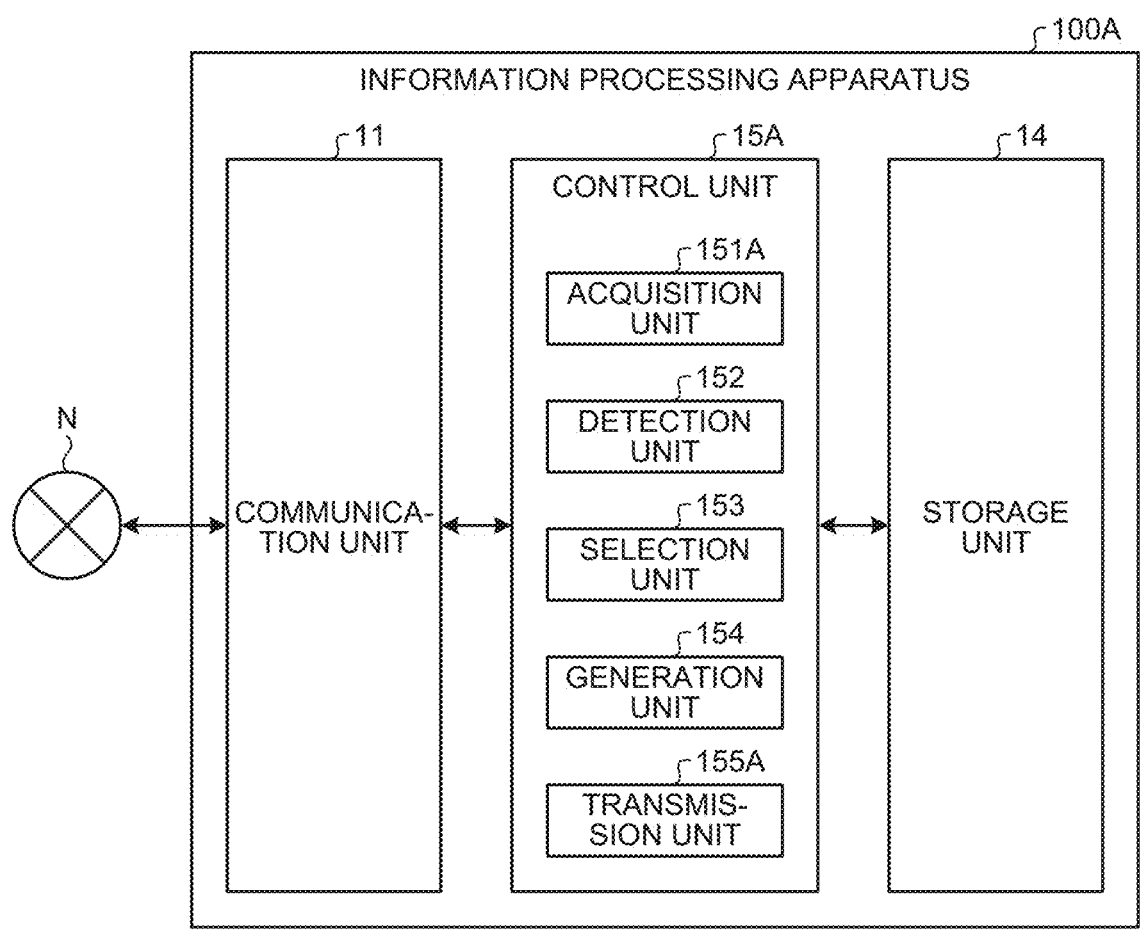
FIG. 17 illustrates a configuration example of an information processing apparatus according to the variation of the present disclosure.

For example, although, in the above-described example, an example in which the information processing apparatus 100 serving as a terminal device used by a user estimates a part of speech has been described, the information processing apparatus that estimates a part of speech and the terminal device used by the user may be separate from each other. This point will be described with reference to FIGS. 16 and 17. FIG. 16 illustrates a configuration example of an information processing system according to a variation of the present disclosure. FIG. 17 illustrates a configuration example of an information processing apparatus according to the variation of the present disclosure.

As illustrated in FIG. 16, an information processing system 1 includes a display device 20, a sensor device 50, and an information processing apparatus 100A. The display device 20, the sensor device 50, and the information processing apparatus 100A are communicably connected by wire or wirelessly via the communication network N. Note that the information processing system 1 in FIG. 16 may include a plurality of display devices 20, a plurality of sensor devices 50, and a plurality of information processing apparatuses 100A. In this case, the information processing apparatus 100A communicates with the display device 20 and the sensor device 50 via the communication network N, provides information to the display device 20, and acquires various pieces of sensor information detected by the sensor device 50. Furthermore, the information processing apparatus 100A acquires user input and an image to be processed with the sensor device 50.

The sensor device 50 includes a sensor similar to the sensor unit 16 of the above-described information processing apparatus 100. The sensor device 50 includes sensors that detect various sensors. For example, the sensor device 50 includes the position/posture sensor 161 and the line-of-sight sensor 162. Furthermore, for example, the sensor device 50 includes a speech sensor that detects a speech, such as a microphone. Note that, when each sensor is individually configured, the information processing system 1 includes a plurality of sensor devices 50. In this case, for example, the information processing system 1 includes a plurality of sensor devices 50 such as a sensor device 50 that detects the position and posture of the user, a sensor device 50 that detects a line of sight of the user, and a sensor device 50 that detects an utterance of the user.

The display device 20 includes a display unit (e.g., liquid crystal display) for displaying various pieces of information. The display device 20 displays information received from the information processing apparatus 100A. The display device 20 displays an image received from the information processing apparatus 100A. The display device 20 displays a selection result received from the information processing apparatus 100A.

Furthermore, the information processing apparatus 100 is a computer that transmits various pieces of information to the display device 20. The information processing apparatus 100 is a server device used to provide service to a user. The information processing apparatus 100A performs information processing similar to that performed by the information processing apparatus 100 except that the information processing apparatus 100A is different from the information processing apparatus 100 in that the information processing apparatus 100A provides information to the display device 20 and acquires information from the terminal device 10. The information processing apparatus 100A is a server that provides service to the display device 20 by using various pieces of sensor information detected by the sensor device 50. For example, the information processing apparatus 100A executes selection processing based on the information detected by the sensor device 50, and transmits the execution result to the display device 20.

As illustrated in FIG. 17, the information processing apparatus 100A includes the communication unit 11, a storage unit 14, and a control unit 15A. The communication unit 11 is connected to the communication network N (e.g., Internet) by wire or wirelessly, and transmits and receives information to and from the display device 20 and the sensor device 50 via the communication network N. In this case, the information processing apparatus 100A is not required to have a function of displaying information as the information processing apparatus 100. Note that the information processing apparatus 100A may include an input unit (e.g., keyboard and mouse) and a display unit (e.g., liquid crystal display) used by an administrator and the like of the information processing apparatus 100A.

The control unit 15A is implemented by, for example, a CPU and an MPU executing a program (e.g., information processing program according to present disclosure) stored in the information processing apparatus 100A using a RAM or the like as a work area. Furthermore, the control unit 15A may be implemented by an integrated circuit such as an ASIC and an FPGA.

As illustrated in FIG. 17, the control unit 15A includes an acquisition unit 151A, the detection unit 152, the selection unit 153, the generation unit 154, and a transmission unit 155A, and implements or executes a function and an action of information processing to be described below. Note that the internal configuration of the control unit 15A is not limited to the configuration in FIG. 17. Another configuration may be adopted as long as the configuration performs the information processing to be described later.

The acquisition unit 151A acquires various pieces of information similarly to the acquisition unit 151. The acquisition unit 151A acquires various pieces of information from the terminal device 10. The acquisition unit 151A acquires various pieces of sensor information from the sensor device 50. The acquisition unit 151A acquires various pieces of information from the storage unit 14.

The transmission unit 155A provides various pieces of information similarly to the transmission unit 155. The transmission unit 155A provides various pieces of information to the display device 20. The transmission unit 155A transmits various pieces of information to the display device 20. The transmission unit 155A provides information generated by the generation unit 154 to the display device 20. The transmission unit 155A provides a detection result from the detection unit 152 to the display device 20. The transmission unit 155A transmits information to be displayed on the display device 20 to the display device 20. The transmission unit 155A transmits a detection result from the detection unit 152 and an image generated by the generation unit 154 to the display device 20.

[2-2. Other Configuration Examples]

Furthermore, the processing according to the embodiment and the variation as described above may be carried out in various different forms (variations) other than the embodiment and variation as described above. For example, the above-described device configuration of the information processing system 1 is merely one example. The information processing system 1 may have any device configuration as long as, for example, selection processing similar to that performed by the information processing apparatus 100 can be performed by the information processing apparatus 100A on a server side.

For example, the information processing system 1 may include a terminal device in which the display device 20 and the sensor device 50 are integrated. In this case, the terminal device is a computer (client terminal) used by the user, and may be implemented by, for example, a notebook PC, a desktop PC, a smartphone, a tablet terminal, a mobile phone, and a PDA.

In this case, the terminal device may be any terminal device as long as the terminal device can transmit information necessary for the information processing apparatus 100A to the information processing apparatus 100A and display information provided from the information processing apparatus 100A. For example, the terminal device may include various devices such as a head-mounted display, VR goggles integrated with a headset, VR goggles fitted in a smartphone, and a wearable device integrated with glasses, earphones, and the like. Note that the above is one example, and the information processing system 1 may be implemented by various configurations.

[2-3. Others]

Furthermore, among pieces of processing described in each of the above-described embodiments, all or part of the processing described as being performed automatically can be performed manually, or all or part of the processing described as being performed manually can be performed automatically by a known method. In addition, the processing procedures, the specific names, and the information including various pieces of data and parameters in the above-described document and drawings can be optionally changed unless otherwise specified. For example, various pieces of information in each figure are not limited to the illustrated information.

Furthermore, each component of each illustrated device is functional and conceptual, and does not necessarily need to be physically configured as illustrated. That is, the specific form of distribution/integration of each device is not limited to the illustrated form, and all or part of the device can be configured in a functionally or physically distributed/integrated manner in any unit in accordance with various loads and use situations.

Furthermore, the above-described embodiments and variations can be appropriately combined as long as the processing contents do not contradict each other.

Furthermore, the effects set forth in the present specification are merely examples and not limitations. Other effects may be exhibited.

3. Effects According to Present Disclosure

As described above, the information processing apparatus (information processing apparatuses 100 and 100A in embodiment) according to the present disclosure includes the acquisition unit (acquisition units 151 and 151A in embodiment) and the selection unit (selection unit 153 in embodiment). The acquisition unit acquires line-of-sight information and object information. The line-of-sight information indicates a gaze point of the user. The object information indicates a plurality of objects. The selection unit selects one object from a plurality of objects based on the positional relation between a gaze point of the user and the plurality of objects.

This enables the information processing apparatus according to the present disclosure to appropriately select an object in accordance with a line of sight of the user by selecting one object from a plurality of objects based on the positional relation between the gaze point of the user and the plurality of objects. Therefore, the information processing apparatus can flexibly select a target in accordance with a line of sight of the user.

Furthermore, the selection unit selects one object, which is an object closest to the gaze point of the user. This causes the information processing apparatus to select an object closest to the gaze point of the user, so that the information processing apparatus can flexibly select a target in accordance with a line of sight of the user even when the line of sight of the user is not stable.

Furthermore, the acquisition unit acquires object information indicating boundaries of a plurality of objects. The selection unit selects a point on a boundary closest to the gaze point of the user in the boundary of the one object. This causes the information processing apparatus to select a boundary of one object closest to the gaze point of the user, so that the information processing apparatus can flexibly select a target in accordance with a line of sight of the user.

Furthermore, the selection unit selects a plurality of points on the boundary of the one object in accordance with movements of the gaze point of the user. This causes the information processing apparatus to select a plurality of points on the boundary of the one object, so that the information processing apparatus can flexibly select a target in accordance with a line of sight of the user.

Furthermore, the information processing apparatus includes a generation unit (generation unit 154 in embodiment). The generation unit generates an area having, as a boundary, a line connecting a plurality of points by connecting the plurality of points in the selected order with a line. This enables the information processing apparatus to generate an area by connecting a plurality of selected points, so that the information processing apparatus can flexibly select (generate) an area in accordance with a line of sight of the user.

Furthermore, the generation unit changes the area by changing the position of one of the plurality of points. This enables the information processing apparatus to change the position of a point after selection, so that the information processing apparatus can flexibly change the selected area with the line of sight of the user.

Furthermore, the generation unit changes the area by adding a new point to the plurality of points. This enables the information processing apparatus to add a new point after generating the area, so that the information processing apparatus can flexibly change the selected area with the line of sight of the user.

Furthermore, the acquisition unit acquires object information indicating boundaries of a plurality of objects detected from an image. This enables the information processing apparatus to appropriately select an object in accordance with a line of sight of the user by using information on the boundaries of the plurality of objects detected from the image. Therefore, the information processing apparatus can flexibly select a target in accordance with a line of sight of the user.

Furthermore, the acquisition unit acquires object information indicating boundaries of a plurality of objects detected from a plurality of images. This enables the information processing apparatus to appropriately select an object in accordance with a line of sight of the user by using information on boundaries of the plurality of objects detected from the plurality of images (layers). Therefore, the information processing apparatus can flexibly select a target in accordance with a line of sight of the user.

Furthermore, the acquisition unit acquires the line-of-sight information and area information. The line-of-sight information indicates a gaze point of the user. The area information indicates a plurality of areas based on the arrangement of the objects. The selection unit selects one area from a plurality of areas based on the positional relation between the gaze point of the user and the plurality of areas. This enables the information processing apparatus to flexibly select a target in accordance with a line of sight of the user even when the line of sight of the user is not stable by selecting an area based on the positional relation between the gaze point of the user and a plurality of areas.

Furthermore, the selection unit selects one area, which is an area where the gaze point of the user is located, from the plurality of areas. This causes the information processing apparatus to select an object closest to the gaze point of the user, so that the information processing apparatus can flexibly select a target in accordance with a line of sight of the user even when the line of sight of the user is not stable.

Furthermore, the acquisition unit acquires area information indicating a plurality of areas based on the boundaries of the objects. The selection unit selects one area corresponding to an object in the boundary of which the gaze point of the user is located. This causes the information processing apparatus to select an area of an object in which the gaze point of the user is located, so that the information processing apparatus can flexibly select a target in accordance with the line of sight of the user.

Furthermore, the selection unit selects the one area as an area to be processed in relation to editing. This enables the information processing apparatus to appropriately select an area desired to be edited, so that the information processing apparatus can flexibly select a target in accordance with a line of sight of the user.

Furthermore, the generation unit generates a mesh that divides one area into a plurality of partial areas. This enables the information processing apparatus to easily select a partial area of the area, so that the information processing apparatus can flexibly change the selected area with the line of sight of the user.

Furthermore, the generation unit generates a mesh that divides one area into a plurality of partial areas having a rectangular shape. This enables the information processing apparatus to easily select a partial area of the area, so that the information processing apparatus can flexibly change the selected area with the line of sight of the user.

Furthermore, the acquisition unit acquires designation information indicating designation of the user for a plurality of partial areas. The selection unit selects a partial area designated by the user from a plurality of partial areas. This enables the information processing apparatus to flexibly select a target in accordance with a line of sight of the user by selecting a partial area designated by the user from the plurality of partial areas in the area.

Furthermore, the acquisition unit acquires designation information indicating designation given by a line of sight of the user for a plurality of partial areas. The selection unit selects a partial area designated by the user based on a line of sight of the user. This enables the information processing apparatus to flexibly select a target in accordance with the line of sight of the user by selecting the partial area with the line of sight of the user.

Furthermore, the acquisition unit acquires designation information indicating designation of a range in one area given by a line of sight of the user. The selection unit selects a partial area located within the range from the plurality of partial areas. This enables the information processing apparatus to flexibly select a target in accordance with the line of sight of the user by selecting the partial area corresponding to a designated range with the line of sight of the user.

4. Hardware Configuration

Figure 18:
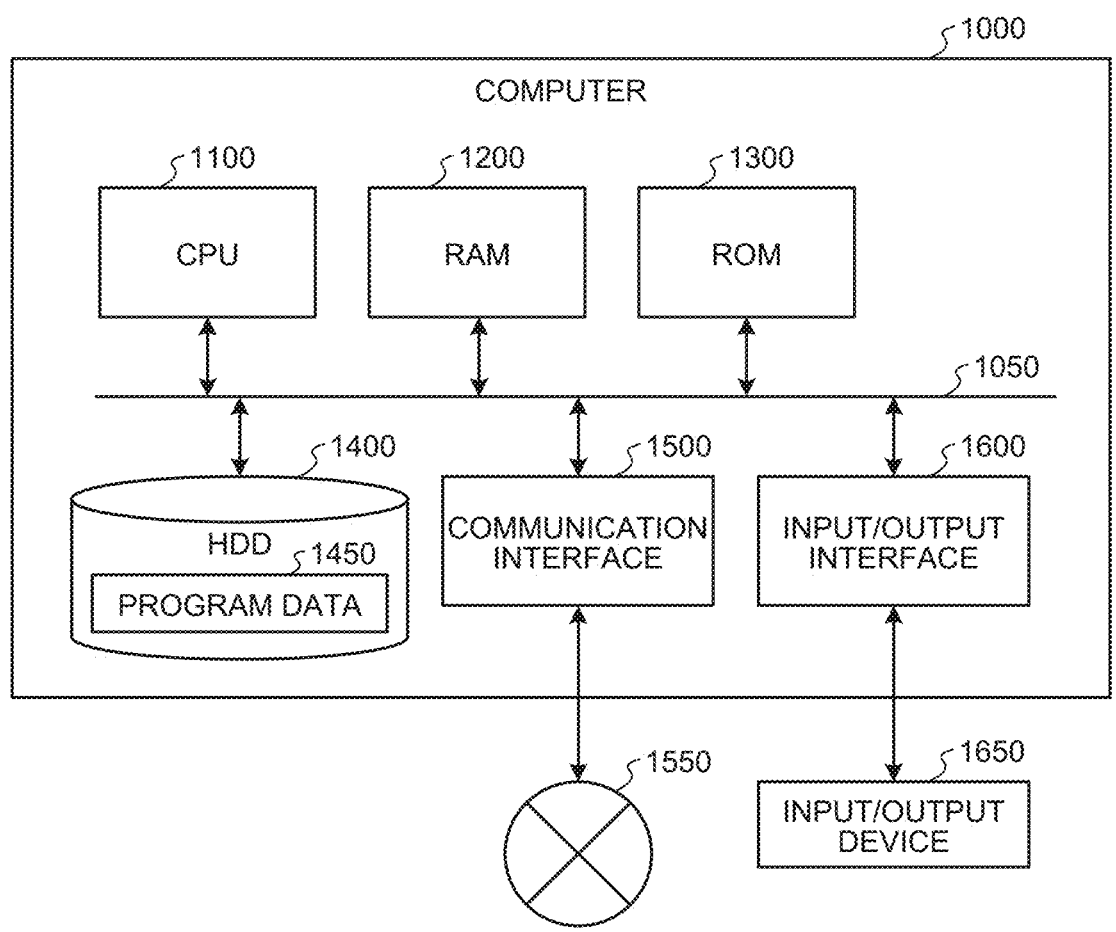
FIG. 18 is a hardware configuration diagram illustrating one example of a computer that implements a function of the information processing apparatus.

An information device such as the information processing apparatuses 100 and 100A according to the above-described embodiment is implemented by a computer 1000 having a configuration as illustrated in FIG. 18, for example. FIG. 18 is a hardware configuration diagram illustrating one example of the computer 1000 that implements the function of the information processing apparatus such as the information processing apparatuses 100 and 100A. An example of the information processing apparatus 100 according to the embodiment will be described below. The computer 1000 includes a CPU 1100, a RAM 1200, a read only memory (ROM) 1300, a hard disk drive (HDD) 1400, a communication interface 1500, and an input/output interface 1600. Each unit of the computer 1000 is connected by a bus 1050.

The CPU 1100 operates based on a program stored in the ROM 1300 or the HDD 1400, and controls each unit. For example, the CPU 1100 develops a program stored in the ROM 1300 or the HDD 1400 on the RAM 1200, and executes processing corresponding to various programs.

The ROM 1300 stores a boot program such as a basic input output system (BIOS) executed by the CPU 1100 at the time when the computer 1000 is started, a program depending on the hardware of the computer 1000, and the like.

The HDD 1400 is a computer-readable recording medium that non-transiently records a program executed by the CPU 1100, data used by the program, and the like. Specifically, the HDD 1400 is a recording medium that records an information processing program according to the present disclosure. The information processing program is one example of a program data 1450.

The communication interface 1500 is used for connecting the computer 1000 to an external network 1550 (e.g., Internet). For example, the CPU 1100 receives data from another device and transmits data generated by the CPU 1100 to another device via the communication interface 1500.

The input/output interface 1600 is used for connecting an input/output device 1650 and the computer 1000 to each other. For example, the CPU 1100 receives data from an input device such as a keyboard and a mouse via the input/output interface 1600. Furthermore, the CPU 1100 transmits data to an output device such as a display, a speaker, and a printer via the input/output interface 1600. Furthermore, the input/output interface 1600 may function as a medium interface that reads a program and the like recorded in a predetermined recording medium (medium). The medium includes, for example, an optical recording medium such as a digital versatile disc (DVD) and a phase change rewritable disk (PD), a magneto-optical recording medium such as a magneto-optical disk (MO), a tape medium, a magnetic recording medium, a semiconductor memory, and the like.

For example, when the computer 1000 functions as the information processing apparatus 100 according to the embodiment, the CPU 1100 of the computer 1000 implements the functions of the control unit 15 and the like by executing an information processing program loaded on the RAM 1200. Furthermore, the HDD 1400 stores the information processing program according to the present disclosure and data in the storage unit 14. Note that the CPU 1100 reads the program data 1450 from the HDD 1400 and executes the program data 1450. In another example, the CPU 1100 may acquire these programs from another device via the external network 1550.

Note that, the present technology can also have the configurations as follows.

(1)
An information processing apparatus comprising:
an acquisition unit that acquires line-of-sight information indicating a gaze point of a user and object information indicating a plurality of objects; and
a selection unit that selects one object from the plurality of objects based on a positional relation between the gaze point of the user and the plurality of objects.

(2)
The information processing apparatus according to (1), wherein the selection unit selects the one object, which is an object closest to the gaze point of the user.

(3)
The information processing apparatus according to (1) or (2),
wherein the acquisition unit acquires the object information indicating boundaries of the plurality of objects, and
the selection unit selects a point on a boundary closest to the gaze point of the user in a boundary of the one object.

(4)
The information processing apparatus according to (3), wherein the selection unit selects a plurality of points on the boundary of the one object in accordance with movement of the gaze point of the user.

(5)
The information processing apparatus according to (4), further comprising
a generation unit that generates an area having, as a boundary, a line connecting the plurality of points by connecting the plurality of points in a selected order with the line.

(6)
The information processing apparatus according to (5), wherein the generation unit changes the area by changing a position of one of the plurality of points.

(7)
The information processing apparatus according to (5) or (6),
wherein the generation unit changes the area by adding a new point to the plurality of points.

(8)
The information processing apparatus according to any one of (3) to (7),
wherein the acquisition unit acquires the object information indicating the boundaries of the plurality of objects detected from an image.

(9)
The information processing apparatus according to (8), wherein the acquisition unit acquires the object information indicating the boundaries of the plurality of objects detected from each of a plurality of images.

(10)
An information processing method comprising pieces of executed processing of:
acquiring line-of-sight information indicating a gaze point of a user and object information indicating a plurality of objects; and
selecting one object from the plurality of objects based on a positional relation between the gaze point of the user and the plurality of objects.

(11)
An information processing apparatus comprising:
an acquisition unit that acquires line-of-sight information indicating a gaze point of a user and area information indicating a plurality of areas based on arrangement of an object; and
a selection unit that selects one area from the plurality of areas based on a positional relation between the gaze point of the user and the plurality of areas.

(12)
The information processing apparatus according to (11), wherein the selection unit selects the one area, which is an area where the gaze point of the user is located, from the plurality of areas.

(13)
The information processing apparatus according to (11) or (12),
wherein the acquisition unit acquires the area information indicating the plurality of areas based on a boundary of an object, and
the selection unit selects the one area corresponding to an object in a boundary of which the gaze point of the user is located.

(14)
The information processing apparatus according to (13), wherein the selection unit selects the one area as an area to be processed in relation to editing.

(15)
The information processing apparatus according to (14), further comprising
a generation unit that generates a mesh that divides the one area into a plurality of partial areas.

(16)
The information processing apparatus according to (15), wherein the generation unit generates the mesh that divides the one area into the plurality of partial areas having a rectangular shape.

(17)
The information processing apparatus according to (15) or (16),
wherein the acquisition unit acquires designation information indicating designation of the user for the plurality of partial areas, and
the selection unit selects a partial area designated by the user from the plurality of partial areas.

(18)
The information processing apparatus according to (17), wherein the acquisition unit acquires the designation information indicating designation given by a line of sight of the user for the plurality of partial areas, and
the selection unit selects a partial area designated by the user based on the line of sight of the user.

(19)
The information processing apparatus according to (17) or (18),
wherein the acquisition unit acquires the designation information indicating designation of a range in the one area given by the line of sight of the user, and the selection unit selects a partial area located in the range from the plurality of partial areas.

(20) An information processing method comprising pieces of executed processing of:

acquiring line-of-sight information indicating a gaze point of a user and area information indicating a plurality of areas based on arrangement of an object; and selecting one area from the plurality of areas based on a positional relation between the gaze point of the user and the plurality of areas.

REFERENCE SIGNS LIST 100, 100A INFORMATION PROCESSING APPARATUS
11 COMMUNICATION UNIT
12 INPUT UNIT
13 DISPLAY UNIT (DISPLAY)
14 STORAGE UNIT
15, 15A CONTROL UNIT
151, 151A ACQUISITION UNIT
152 DETECTION UNIT
153 SELECTION UNIT
154 GENERATION UNIT
155, 155A TRANSMISSION UNIT
16 SENSOR UNIT
161 POSITION/POSTURE SENSOR
162 LINE-OF-SIGHT SENSOR
20 DISPLAY DEVICE
50 SENSOR DEVICE

The invention claimed is:

1. An information processing apparatus comprising:
a control unit configured to
acquire line-of-sight information indicating a gaze point of a user and object information indicating a plurality of objects; and
select one object from the plurality of objects based on a positional relation between the gaze point of the user and the plurality of objects, wherein the control unit is further configured to
acquire the object information indicating boundaries of the plurality of objects, and
select a point on a boundary closest to the gaze point of the user in a boundary of the one object.

2. The information processing apparatus according to claim 1, wherein
the control unit is further configured to select the one object, which is an object closest to the gaze point of the user.

3. The information processing apparatus according to claim 1, wherein
the control unit is further configured to select a plurality of points on the boundary of the one object in accordance with movement of the gaze point of the user.

4. The information processing apparatus according to claim 3, wherein
the control unit is further configured to generate an area having a boundary indicated by a line connecting the plurality of points in an order that the plurality of points was selected.

5. The information processing apparatus according to claim 4, wherein
the control unit is further configured to change the area by changing a position of one of the plurality of points.

6. The information processing apparatus according to claim 4, wherein
the control unit is further configured to change the area by adding a new point to the plurality of points.

7. The information processing apparatus according to claim 1, wherein
the control unit is further configured to acquire the object information indicating the boundaries of the plurality of objects detected from an image.

8. The information processing apparatus according to claim 7, wherein
the control unit is further configured to acquire the object information indicating the boundaries of the plurality of objects detected from each of a plurality of images.

9. An information processing method to be executed by an information processing apparatus, the method comprising:
acquiring line-of-sight information indicating a gaze point of a user, and object information indicating a plurality of objects and boundaries of the plurality of objects;
selecting one object from the plurality of objects based on a positional relation between the gaze point of the user and the plurality of objects; and
selecting a point on a boundary closest to the gaze point of the user in a boundary of the one object.

10. An information processing apparatus comprising:
control unit configured to
acquire line-of-sight information indicating a gaze point of a user and area information indicating a plurality of areas based on arrangement of objects; and
select one area from the plurality of areas based on a positional relation between the gaze point of the user and the plurality of areas, wherein
the control unit is further configured to
acquire the area information indicating the plurality of areas based on boundaries of the objects, and
select the one area corresponding to one of the objects that has a boundary in which the gaze point of the user is located.

11. The information processing apparatus according to claim 10, wherein
the control unit is further configured to select the one area, which is an area where the gaze point of the user is located, from the plurality of areas.

12. The information processing apparatus according to claim 10, wherein
the control unit is further configured to select the one area as an area to be processed in relation to editing.

13. The information processing apparatus according to claim 12, wherein
the control unit is further configured to generate a mesh that divides the one area into a plurality of partial areas.

14. The information processing apparatus according to claim 13, wherein
the control unit is further configured to generate the mesh that divides the one area into the plurality of partial areas each having a rectangular shape.

15. The information processing apparatus according to claim 13, wherein
the control unit is further configured to acquire designation information indicating designation of the user for the plurality of partial areas, and select a partial area designated by the user from the plurality of partial areas.

16. The information processing apparatus according to claim 15, wherein
the control unit is further configured to acquire the designation information indicating designation given by a line of sight of the user for the plurality of partial areas, and select a partial area designated by the user based on the line of sight of the user.

17. The information processing apparatus according to claim 15, wherein
the control unit is further configured to acquire the designation information indicating designation of a range in the one area given by a line of sight of the user, and select a partial area located in the range from the plurality of partial areas.

* * * * *